US008148331B2

(12) United States Patent
Rathore et al.

(10) Patent No.: US 8,148,331 B2
(45) Date of Patent: Apr. 3, 2012

(54) METHOD FOR THE PREPARATION OF GROWTH HORMONE AND ANTAGONIST THEREOF HAVING LOWER LEVELS OF ISOFORM IMPURITIES THEREOF

(75) Inventors: Anurag S. Rathore, Thousand Oaks, CA (US); Stephen B. Lyle, Marcellus, MI (US); David E. Steinmeyer, Clarkson Valley, MO (US); Scott I. Allen, St. Peters, MO (US); John Meyer, Ellisville, MO (US); Denis M. Boyle, Marthasville, MO (US); John J. Buckley, Ofallon, MO (US); Gary V. Johnson, St. Charles, MO (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 12/405,857

(22) Filed: Mar. 17, 2009

(65) Prior Publication Data

US 2010/0021966 A1    Jan. 28, 2010

Related U.S. Application Data

(63) Continuation of application No. 10/646,798, filed on Aug. 25, 2003, now abandoned.

(60) Provisional application No. 60/406,553, filed on Aug. 28, 2002.

(51) Int. Cl.
*A61K 38/16* (2006.01)
*A61K 38/27* (2006.01)
*A61K 39/385* (2006.01)

(52) U.S. Cl. ... 514/21.2; 514/5.1; 514/11.3; 424/195.11

(58) Field of Classification Search .......................... None
See application file for complete search history.

(56) References Cited

U.S. PATENT DOCUMENTS

| 5,849,535 | A * | 12/1998 | Cunningham et al. | ....... 435/69.4 |
| 6,057,292 | A | 5/2000 | Cunningham et al. | ........... 514/12 |
| 7,470,779 | B2 * | 12/2008 | Boyle et al. | ................... 530/416 |
| 2001/0005750 | A1 * | 6/2001 | Castan | ........................ 536/23.5 |

FOREIGN PATENT DOCUMENTS

| WO | WO 9424157 | 10/1994 |
| WO | WO 9602570 | 2/1996 |
| WO | WO 0002900 | 1/2000 |
| WO | WO 02057478 | 7/2002 |
| WO | WO 2004031213 | 4/2004 |

OTHER PUBLICATIONS

Thomsen, 1994, Pharmacology and Toxicology, 74, 351-358.*
Andersson, et al., "Isolation and characterization of a trisulfide variant of recombinant human growth hormone formed during expression in *Escherichia coli*", International Journal of Peptide Protein Research, 1996, pp. 311-321, vol. 47.
Houk, J., et al., "Structure-Reactivity Relations for Thiol-Disulfide Interchange[1]", Journal of American Chemistry Society, 1987, pp. 6825-6836, vol. 109, No. 22.
Jesperson, A., et al., "Characterisation of a trisulphide derivative of biosynthetic human growth hormone produced in *Escherichia coli*", Eur. J. Biochem., 1994, pp. 365-373, vol. 219.
Jorgensen, et al., "Quantifying biosynthetic human growth hormone in *Escherichia coli* with capillary electrophoresis under hydrophobic conditions", Journal of Chromatography A, 1998, pp. 205-214, vol. 817.
The Merck Index, 12th Edition, S. Budavari (Editor), Merck & Co., Inc., Therapeutic Category and Biological Activity Index, p. THER-19 (under "Chelating Agent"), Whitehouse Station, NJ 1996.

* cited by examiner

*Primary Examiner* — Cecilia J Tsang
*Assistant Examiner* — Satyanarayana R Gudibande
(74) *Attorney, Agent, or Firm* — Cregg C. Benson; Ian J. S. Lodovice

(57) ABSTRACT

The present invention is directed generally to recombinant methods for making a desired polypeptide. These method(s) yield a polypeptide product containing reduced levels of isoform impurities thereof. In particular, the present invention is directed to (1) a recombinant method for preparing growth hormone with reduced isoform impurities thereof and (2) a recombinant method for preparing a growth hormone antagonist, such as pegvisomant, and its protein intermediate, also having reduced isoform impurities thereof. More specifically, the isoform impurities that are decreased by methods of the present invention are the trisulfide and des-phe isoform impurities of growth hormone and growth hormone antagonist (or its intermediate), respectively.

22 Claims, 12 Drawing Sheets

B-2036

(Trisulfide Isoform Impurity of B-2036)

FIG. 3E

*Flowchart 2 Process Flow Diagram for Recovery & Purification to B-2036 (Bulk Intermediate)*

| UNIT OPERATION | PROCESS DESCRIPTION | PROCESS CONTROLS |
|---|---|---|
| ↓ | | |
| B-2036 Bulk Intermediate | Filter: Sartobran P 0.45/0.2 µ<br>Container: 2L Teflon Bottles (Nalgene)<br>Fill Volume: ~ 1.8 L<br>Temperature: -70°C | Yield (w/UF/DF): >/= 85%<br>Filtrate: Appearance, pH, Tryptic Map, IEXHPLC, SEHPLC, RPHPLC, SDS-PAGE, UV, LAL, Bioburden, DNA, Host Cell Protein |

METHOD FOR THE PREPARATION OF GROWTH HORMONE AND ANTAGONIST THEREOF HAVING LOWER LEVELS OF ISOFORM IMPURITIES THEREOF

CROSS-REFERENCE TO RELATED APPLICATION

This application is a continuation of U.S. patent application Ser. No. 10/646,798, filed Aug. 25, 2003, which is a Request for Continued Examination of U.S. patent application Ser. No. 10/646,798, filed Aug. 25, 2003 which claims the priority benefit of U.S. Provisional Patent Application No. 60/406,553, filed Aug. 28, 2002, all of which are incorporated herein in their entireties by reference.

FIELD OF THE INVENTION

The present invention is directed generally to recombinant methods for making a desired polypeptide. These method(s) yield a polypeptide product containing reduced levels of isoform impurities thereof. In particular, the present invention is directed to (1) a recombinant method for preparing growth hormone with reduced isoform impurities thereof and (2) a recombinant method for preparing a growth hormone antagonist, such as pegvisomant, and its protein intermediate, also having reduced isoform impurities thereof. More specifically, the isoform impurities that are decreased by methods of the present invention are the trisulfide and des-phe isoform impurities of growth hormone and growth hormone antagonist (or its intermediate), respectively.

BACKGROUND OF THE INVENTION

Pegvisomant (Somavert®; Pharmacia Corp.) is a human growth hormone receptor antagonist. It is an analog of human growth hormone ("hGH") that has been structurally altered. The amino acid sequence of the protein component/intermediate (B-2036) of pegvisomant differs from the amino acid sequence of hGH at nine positions. The specific amino acid substitutions are as follows: H18D, H21N, G120K, R167N, K168A, D171S, K172R, E174S, and I179T. As is well recognized in the art, the first letter (i.e., H18D) represents the amino acid in the sequence of hGH at the numbered position (i.e., $18^{th}$ amino acid position as indicated by H18D) which is substituted with the amino acid designated by the second letter (i.e., H18D). Therefore, H18D designates a substitution of the amino acid his by the amino acid asp at the $18^{th}$ amino acid position of the wild-type hGH amino acid sequence.

FIG. 1A schematically shows the amino acid sequence structure of the protein component/intermediate (B-2036) of pegvisomant (PEG B-2036) with asterisks indicating the potential sites of polyethylene glycol polymer ("PEG" unit) attachment. Additionally, the amino acid sequence listing of the protein component/intermediate (B-2036—without PEG unit attachment) of pegvisomant is identified herein as SEQ. ID. NO. 1. For comparison, the amino acid sequence listing of human growth hormone is identified herein as SEQ. ID. NO. 2. Both sequence listings are provided herewith. See also Jorgensen et al., "Quantifying biosynthetic human growth hormone in *Escherichia coli* with electrophoresis under hydrophobic conditions," J. Chromatography A 817:205-214 (1998) for the sequence of hGH.

Structurally, pegvisomant is a protein (containing 191 amino acid residues) to which predominantly 4 to 6 PEG units are covalently bound. The molecular weight of the protein component/intermediate (B-2036) of pegvisomant is 21,998 Daltons. The molecular weight of each PEG unit of pegvisomant is approximately 5000 Daltons. Thereby the predominant molecular weights of pegvisomant are approximately 42,000 (4 PEG units/molecule), 47,000 (5 PEG units/molecule) and 52,000 (6 PEG units/molecule) Daltons.

Referring to the agonist, and without being bound by theory, it is believed that endogenous hGH activates its receptors when a single hGH molecule binds to two of its adjacent (and identical) receptor molecules, inducing hormone-mediated receptor homodimerization. See U.S. Pat. Nos. 5,849,535 and 6,057,292. The activity of hGH depends on its ability to bind two of its adjacent (and identical) receptors across two separate binding sites (site 1 and site 2) on the same hGH molecule. These hGH binding sites, designated as site 1 and site 2, are numbered 1 and 2 to reflect the order of their binding to two adjacent (and identical) hGH receptors which mediate hGH-dependent homodimerization.

Further, without being bound by theory, it is believed that pegvisomant selectively binds to human growth hormone receptors ("GH receptors") on cell surfaces, where it blocks the binding of endogenous human growth hormone, thereby interfering with human growth hormone signal transduction. The structural modifications to the protein portion (also called "component" or "intermediate") of pegvisomant (relative to hGH) allow pegvisomant to competitively block interaction between an hGH molecule and an hGH receptor. Pegvisomant binds to the GH receptor, therefore, blocking GH binding since the receptor is occupied. The structural modifications prevent receptor dimerization, as a result signal transduction does not occur. By so blocking the required close interaction between an hGH molecule and an hGH receptor, pegvisomant blocks the hGH-mediated homodimerization of the hGH receptors, giving pegvisomant its antagonist activity.

This antagonist is used to treat conditions, including, but not limited to, acromegaly in patients who do not adequately respond to surgery, radiation therapy, and/or other conventional medical therapies, or who cannot otherwise tolerate these therapies. In addition, the structural modifications to the protein portion (B-2036) of pegvisomant cause it to exhibit a binding affinity for the prolactin receptor which is lower than that of hGH, thereby minimizing the undesirable lactation-related side effects associated with the use of pegvisomant.

The protein intermediate portion (B-2036) of pegvisomant is synthesized by a strain of *Escherichia coli* bacteria that has been genetically modified by the addition of a plasmid that carries a gene for the growth hormone receptor antagonist (B-2036). B-2036 is then recovered from the microbial cells and purified. The purified B-2036 is then pegylated to produce pegvisomant (PEG B-2036). U.S. Pat. Nos. 5,849,535 and 6,057,292 describe methods of making B-2036 and methods for conjugating one or more PEG units to B-2036, albeit without details as to how to decrease, reduce, eliminate, reverse and/or prevent the formation of unacceptably high levels of the trisulfide and des-phe isoform impurities thereof.

One of the problems encountered using conventional recombinant manufacturing methods to make B-2036 is the formation of its isoform impurities, such as its des-phe and the trisulfide isoforms. The des-phe isoform impurity is one wherein the B-2036 molecule is missing its amino-terminal phenylalanine. See FIG. 1A depicting the subject amino-terminal phenylalanine residue (i.e., indicated by the letter "F") adjacent the —$NH_2$ end of B-2036. The trisulfide isoform impurity is one wherein the B-2036 molecule contains an extra sulfur atom that forms a "trisulfide bridge" within the molecule. See box in FIG. 1B. Also, see Andersson et al., "Isolation and characterization of a trisulfide variant of recombinant human growth hormone formed during expression in *Escherichia coli*," Int. J. Peptide Protein Res. 47:311-321 (1996) and A. Jesperson et al., "Characterisation of a trisulphide derivative of biosynthetic human growth hormone produced in *Escherichia coli*," Eur. J. Biochem. 219:365-373 (1994). Without being bound by theory, it is believed that these isoform impurities typically are generated during cell growth (e.g., fermentation) and expression (synthesis and secretion) of B-2036 in genetically modified host cells, and/or during extraction and purification of the B-2036 protein.

Regarding certain impurities, International Application WO 94/24157 (published Oct. 27, 1994) discloses a hydrophobic derivative of hGH comprising an extra sulfur atom as compared to the native hGH. See WO 94/24157 at page 3, lines 3-10. The extra sulfur atom of the hydrophobic derivative of hGH forms a "trisulfide bridge" yielding an hGH trisulfide variant. See WO 94/24157 at page 7, lines 11-16. The WO 94/24157 reference further states that this hGH trisulfide variant can be converted back to its native hGH form by treating the hGH trisulfide variant with a mercapto compound such as cysteine, glutathione, 2-mercapto ethanol or dithiothreitol. See WO 94/24157 at pages 4 and 5.

International Application WO 96/02570 (published Feb. 1, 1996) describes another method for converting the hGH trisulfide variant back to its native form using either sodium sulfite, potassium sulfite, ammonium sulfite, or an alkaline-earth metal sulfite such as magnesium sulfite or calcium sulfite. See WO 94/24157 at page 4, lines 17-21.

International Application WO 00/02900 (published Jan. 20, 2000) entitled "Method for the production of recombinant peptides with a low amount of trisulfides" discusses "a method for the reduction of the amount of trisulfides in the production of recombinant peptides, e.g., both proteins and smaller peptides. The invention is based on the novel and unexpected finding that the amount of trisulfides in the production of recombinant peptides could be reduced by the addition of a metal salt, preferably in excess, already during or after fermentation and not, as earlier suggested, by conversion of the formed trisulfides of growth hormone into the native form." (Emphasis added.) See WO 00/02900 at page 2, lines 21-27. The WO 00/02900 reference further states "[t]he protein can be any recombinant protein but is preferably recombinant growth hormone which can be both human and animal such as human growth hormone (hGH), bovine growth hormone (bGH) and porcine growth hormone (pGH)." (Emphasis added.) See WO 00/02900 at page 3, lines 4-6.

International Application No. WO 02/057478 (published Jul. 25, 2002) entitled "Methods and Composition For Extracting Proteins From Cells" is directed to a method of releasing a protein from a host cell by contacting the host cell with a reducing agent and a detergent. The reference states that the purpose of the reducing agent is to "facilitate[ ] the recovery of proteins in their native conformations." See WO 02/057478 at page 2, lines 16-18. Furthermore, WO 02/057478 describes that the "one or more reducing agents are agents . . . that reduce disulfide bonds and/or maintain sulfhydryl residues in the[ir] reduced form. Any such reducing agent or agents may be used. In a preferred embodiment, the one or more reducing agents used are selected from the group consisting of, dithiothrietol (DTT); dithioerythritol (DTE); Cysteine (Cys) and Tris 2-carboxyethyphosphine (TCEP)." (Emphasis added.) See WO 02/057478 from page 3, line 24 to page 4, line 4.

The above-noted references, however, are silent with regard to the prevention, reversal, reduction, or elimination of isoform impurity formation associated with a growth hormone antagonist such as pegvisomant or its protein portion, B-2036. Accordingly, there is a need for improved methods of making B-2036 that decrease, attenuate, prevent, minimize, reverse and/or eliminate the formation of its isoform impurities (trisulfide and/or des-phe). Likewise, these references also are silent as to the detection, attenuation, minimization, reversal, reduction or elimination of the formation of the des-phe isoform impurity of growth hormone. Accordingly, there is a need for improved methods of making growth hormone that decrease, attenuate, prevent, minimize, reverse and/or eliminate the formation of its des-phe isoform impurity.

SUMMARY OF THE INVENTION

Figure 1A:
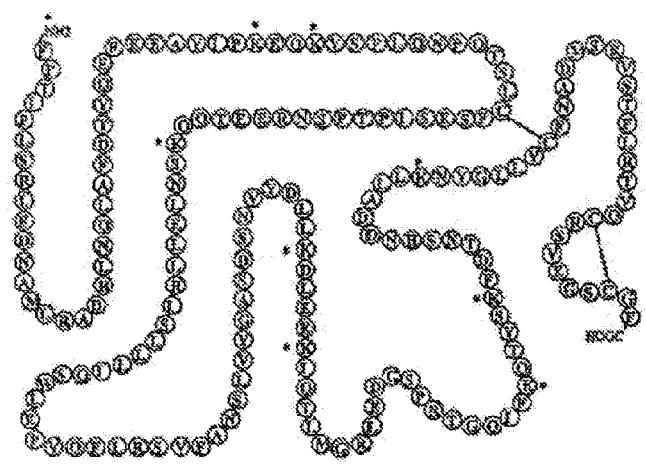
FIG. 1A depicts the amino acid sequence of B-2036 which corresponds to SEQ. ID. NO. 1. The asterisks (*) in FIG. 1A indicate nine (9) potential sites for covalent attachment of PEG units to each molecule of B-2036. Note that while nine (9) possible sites are identified, not all 9 sites have to be covalently bound to PEG units. Preferably, there are 4-6 PEG units per B-2036 molecule.

In view of the foregoing need to provide an improved process for making a recombinant growth hormone agonist, a recombinant human growth hormone agonist, a recombinant growth hormone antagonist, and/or a recombinant human growth hormone antagonist, with decreased levels of undesirable isoform impurities thereof, the present invention is directed to an improved processes or for producing recombinant growth hormone (including, but not limited to, human growth hormone) and recombinant growth hormone antagonist (including, but not limited to, human growth hormone antagonist) with decreased levels of their des-phe and/or trisulfide isoform impurities.

With regard to recombinant growth hormone (including, but not limited to hGH), formation of its des-phe isoform impurity is decreased by sufficient addition of (1) a chelating agent or (2) a metal salt, respectively.

With regard to recombinant growth hormone antagonist (including, but not limited to, human growth hormone antagonist), its trisulfide isoform impurity is decreased by sufficient contact between the trisulfide isoform impurity and (1) a mercapto compound, (2) a chelating agent, (3) a metal salt, (4) a mercapto compound together with a metal salt, or (5) a mercapto compound after contact with a chelating agent but in the absence of the chelating agent, respectively.

With regard to recombinant growth hormone antagonist (including, but not limited to, human growth hormone antagonist), formation of its des-phe isoform impurity is decreased by addition of (1) a chelating agent or (2) a metal salt, respectively.

DETAILED DESCRIPTION OF THE PREFERRED EMBODIMENTS

The terms "growth hormone antagonist" and "growth hormone receptor antagonist" include (but are not limited to) polypeptides that inhibit or otherwise antagonize the binding of growth hormone to its growth hormone receptor to block the biological effect(s) of growth hormone. Preferably, the "growth hormone antagonist" or the "growth hormone receptor antagonist" is B-2036 or a variant thereof. Such "variants" include, but are not limited to, homologues (particularly homologues with conservative amino acid substitutions, additions or deletions relative to B-2036), analogues, fragments, pseudopeptides, antibodies, etc. thereof (respectively) having growth hormone receptor antagonist activity.

The terms "growth hormone agonist" and "growth hormone receptor agonist" include (but are not limited to) polypeptides that bind to and activate its growth hormone receptor. Preferably, the "growth hormone agonist" or the "growth hormone receptor agonist" is human growth hormone or a variant thereof. Such "variants" include, but are not limited to, homologues (particularly homologues with conservative amino acid substitutions, additions or deletions relative to human growth hormone), analogues, fragments, pseudopeptides, antibodies, etc. (respectively) having growth hormone receptor agonist activity.

The term "GROWTH HORMONE AND ANTAGONIST THEREOF" refers to growth hormone agonist (i.e., "GROWTH HORMONE") and growth hormone antagonist (i.e., "AND ANTAGONIST THEREOF").

The term "and" may mean "and" or "or" as appropriate or necessary to recite a process to yield the desired decrease in the level of the relevant impurity (e.g., trisulfide or des-phe isoform impurity).

The term "or" may mean "and" or "or" as appropriate or necessary to recite a process to yield the desired decrease in the level of the relevant impurity (e.g., trisulfide or des-phe isoform impurity).

As used herein, unless indicated otherwise, the term "decrease" (or apparent variations thereof) means to eliminate, minimize, reduce, prevent and/or attenuate the amount of the relevant isoform impurity, whether it be the trisulfide isoform impurity or the des-phe isoform impurity.

Unless indicated otherwise, the term "host cell" (or apparent variations thereof) refers to any host cell in which recombinant B-2036 or recombinant hGH may be formed. Accordingly, the host cell may be a mammalian host cell, a plant host cell, or a microbial host cell such as E. coli. or even yeast cells. It is important to note that the host cell be one that is sufficient to grow the desired recombinant B-2036 protein component or recombinant hGH therein. As such, there is no limitation as to what the host cell may be except that it be one capable of recombinantly producing the B-2036 protein component or recombinant hGH of interest or "variants" thereof.

Furthermore, as used herein, unless otherwise indicated, the term "growing" (or apparent variations thereof, e.g., growth) includes, but is not limited to, fermenting and culturing, or otherwise causing the host cell(s) to proliferate sufficiently to produce desired amounts of the recombinant B-2036 protein component or recombinant hGH.

Further, while the present invention is described with respect to recombinant B-2036, and recombinant PEG B-2036, unless indicated otherwise, it is understood that the subject invention may be used with any recombinant growth hormone agonist, recombinant growth hormone antagonist, whether it be mammalian growth hormone or its antagonist, human growth hormone or its antagonist, or bovine growth hormone or its antagonist, etc.

Pegvisomant (PEG B-2036) is the pegylated form of recombinant protein (B-2036) produced in recombinant host cells (e.g., recombinant, genetically modified E. coli. host cells). The B-2036 protein is produced during cell growth (e.g., by fermentation) and expression (synthesis and secretion). After its production, B-2036 is isolated (e.g., by homogenization) followed by purification (e.g., by extraction, centrifugation, reverse phase and anion-exchange chromatography, and buffer exchange). However, as noted during recombinant production of the B-2036 protein, undesirable isoform impurities of B-2036 are formed, which are the trisulfide and the des-phe isoform impurities of B-2036.

As noted, FIG. 1A illustrates the amino acid sequence of B-2036 with the standard 1-letter abbreviations indicating which amino acid is present at each lettered position. For reference, see Table 1 below indicating the correspondence between the letter and its associated amino acid.

TABLE 1

| Polypeptide Amino Acid |
|---|
| Ala (A) |
| Glu (E) |
| Gln (Q) |
| Asp (D) |
| Asn (N) |
| Leu (L) |
| Gly (G) |
| Lys (K) |
| Ser (S) |
| Val (V) |
| Arg (R) |
| Thr (T) |
| Pro (P) |
| Ile (I) |
| Met (M) |
| Phe (F) |
| Tyr (Y) |
| Cys (C) |
| Trp (W) |
| His (H) |

Additionally, the amino acid sequence of B-2036 is provided herein as SEQ. ID. NO. 1 and the amino acid sequence hGH is provided herein as SEQ. ID. NO. 2.

1. Recombinant Growth Hormone Antagonist and its Trisulfide Isoform Impurity

Figure 1B:
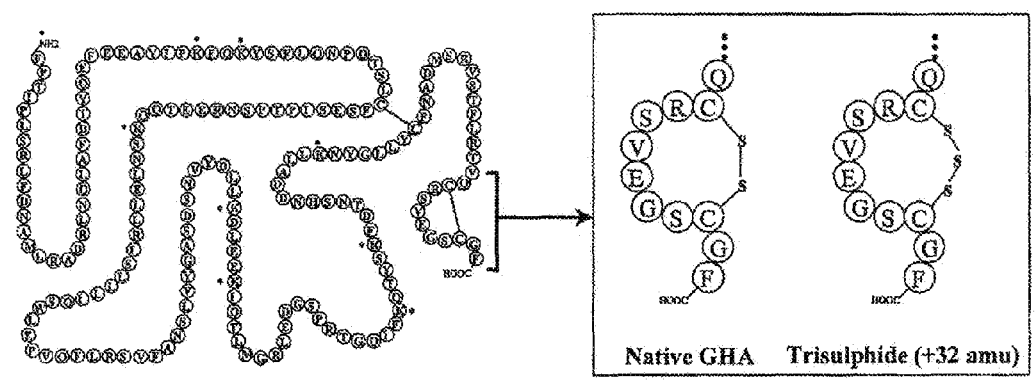
FIG. 1B depicts the structure of the trisulfide isoform impurity of B-2036 (designated "Trisulphide (+32 amu")) as compared to its desirable form (designated "Native GHA").
Figure 2A:
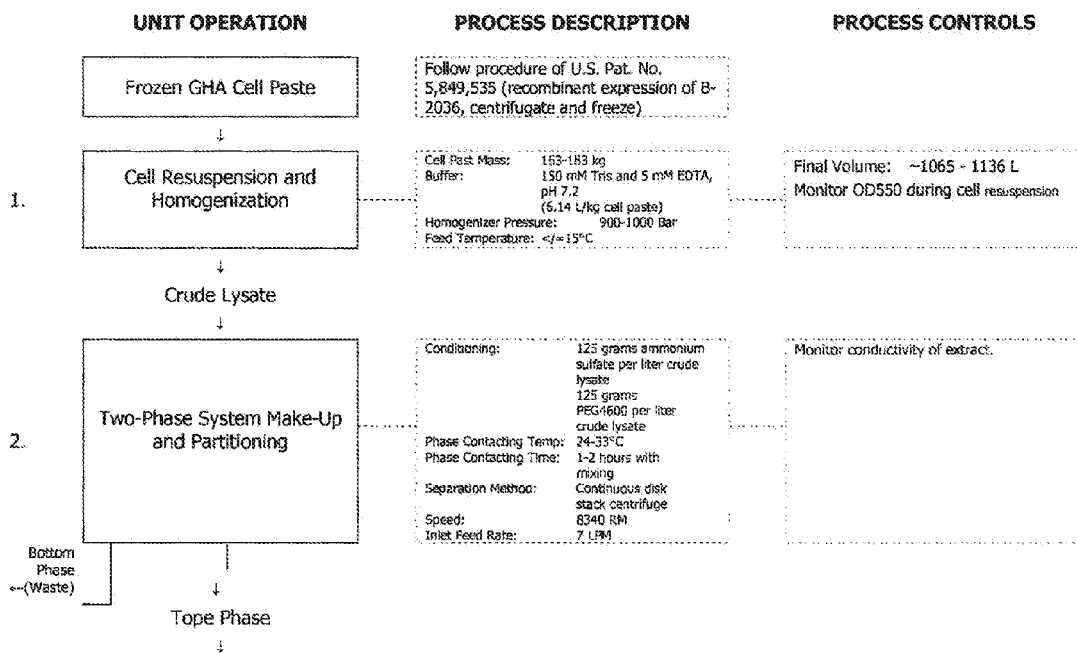
FIG. 2 depicts Flowchart 1 a process flow diagram for recovery & purification to B-2036 (Bulk Intermediate).
Figure 2B:
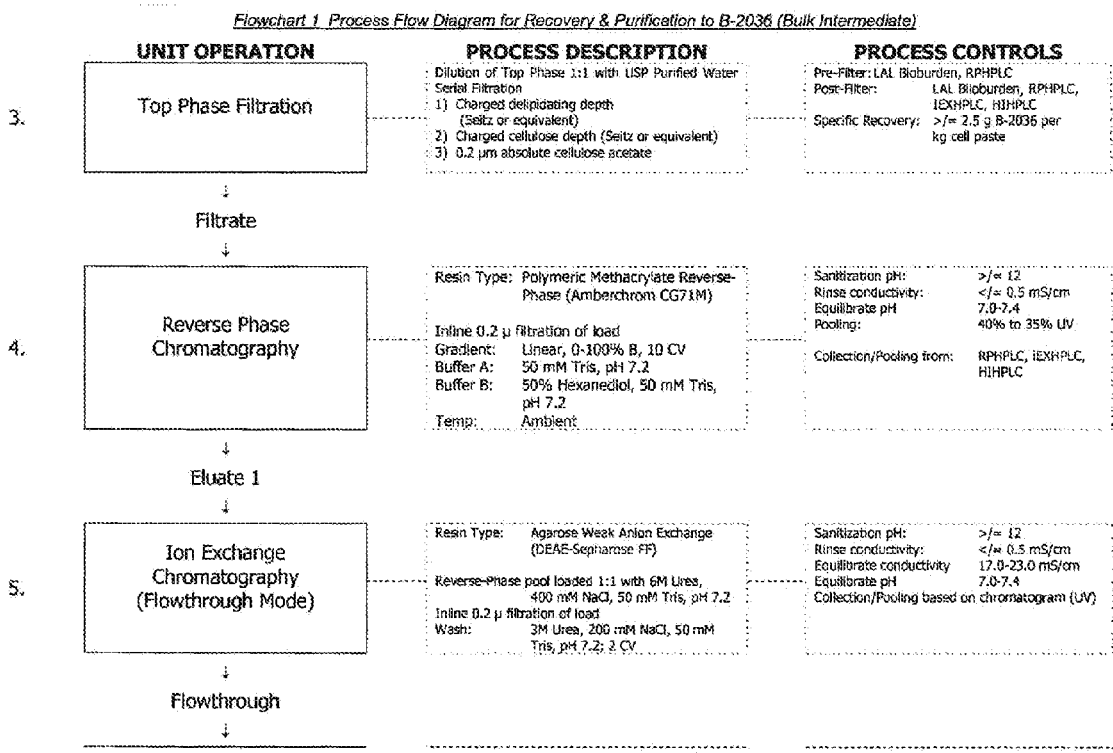
Figure 2C:
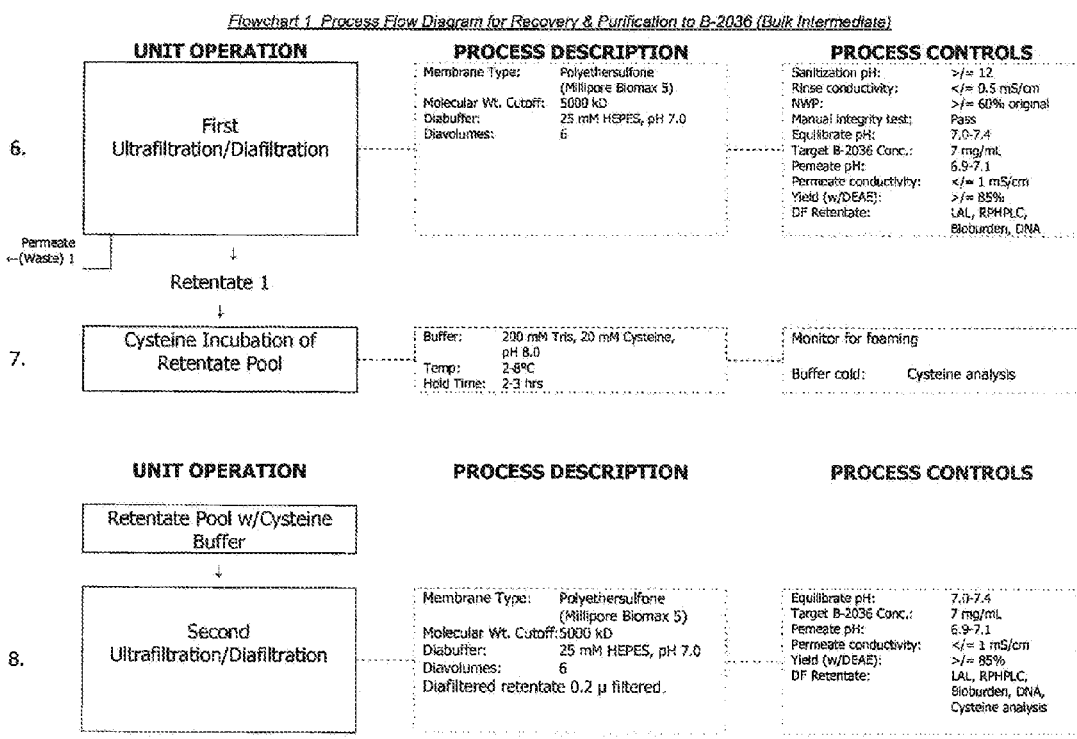
Figure 2D:
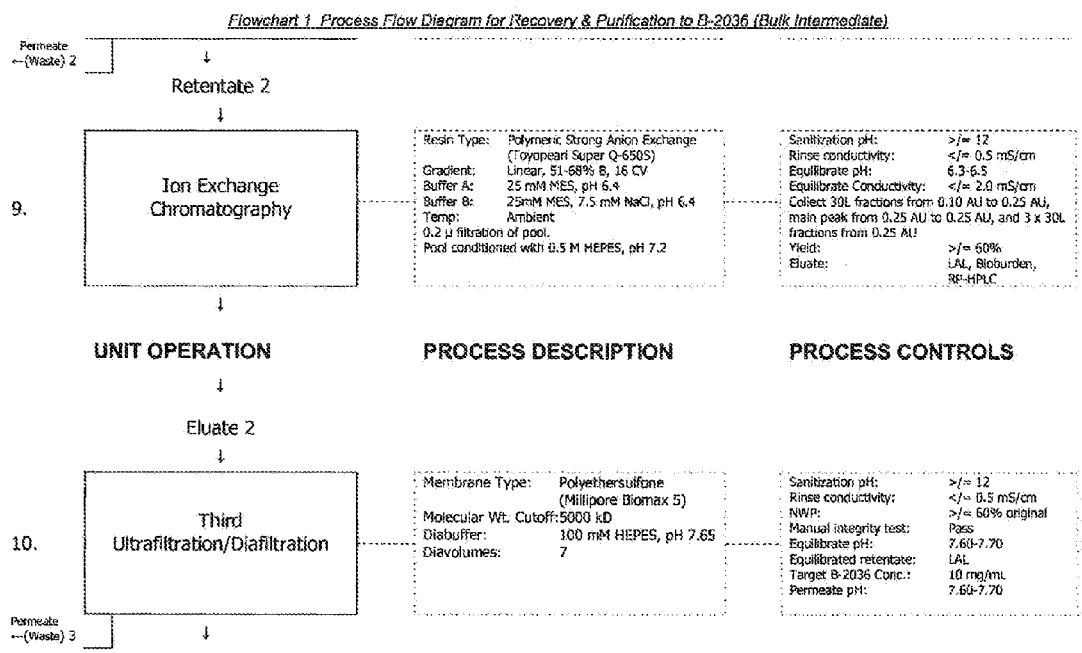
Figure 2E:
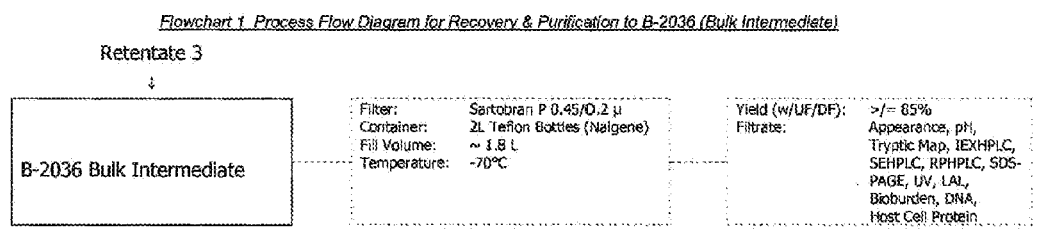
Figure 3A:
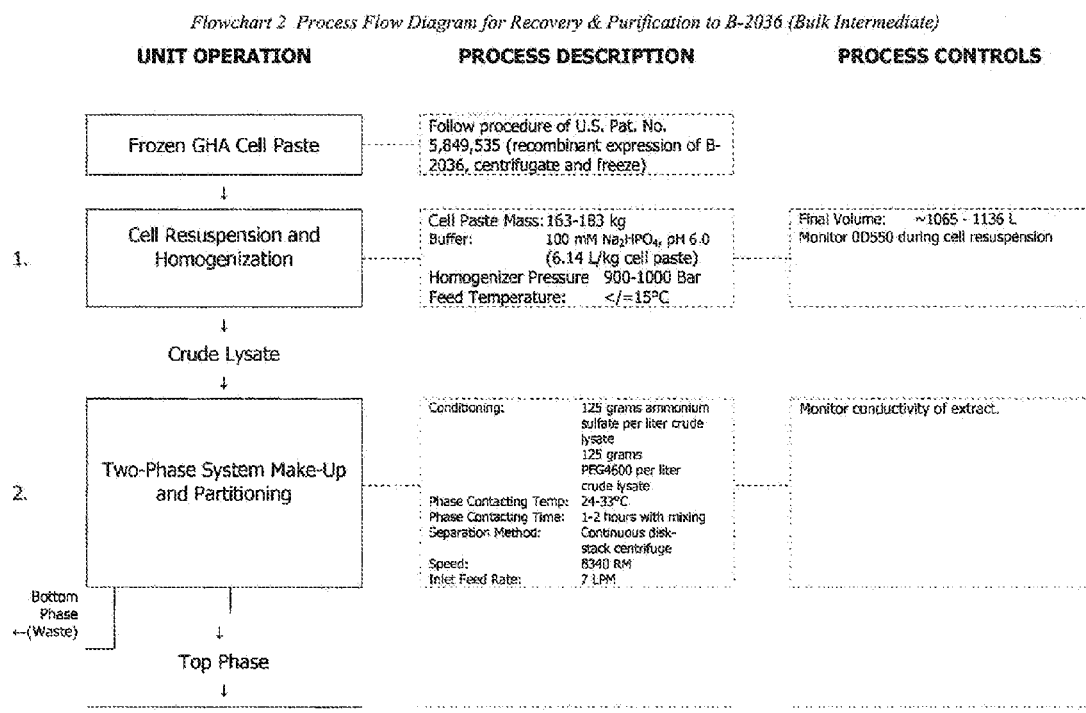
FIG. 3 depicts Flowchart 2 a process flow diagram for recovery & purification to B-2036 (Bulk Intermediate).
Figure 3B:
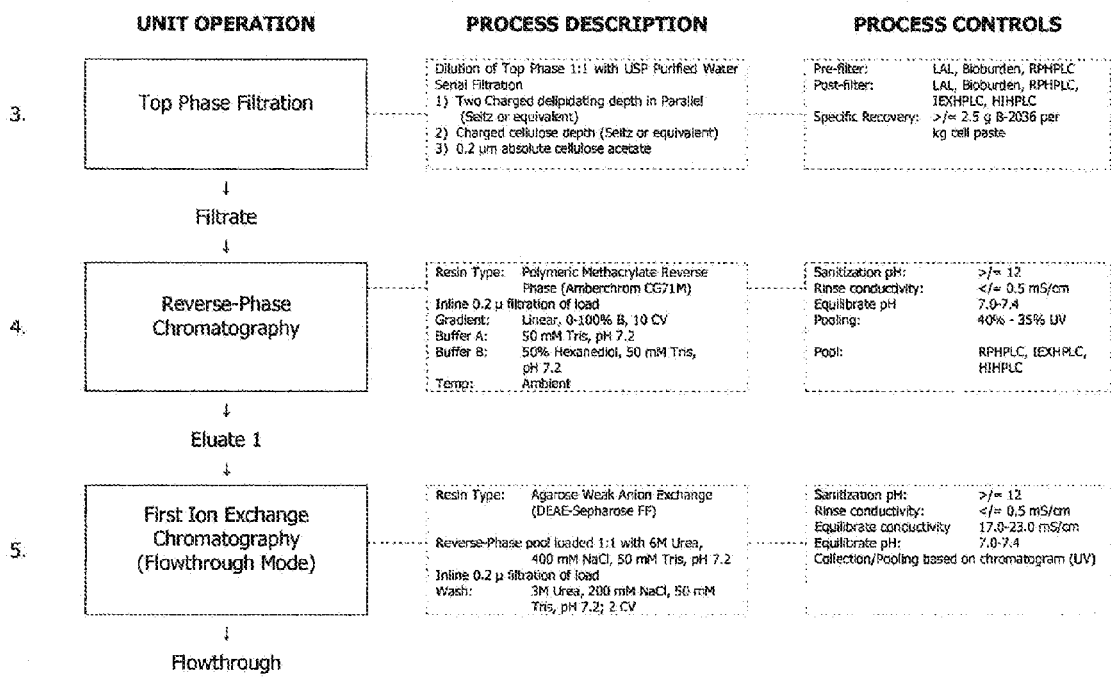
Figure 3C:
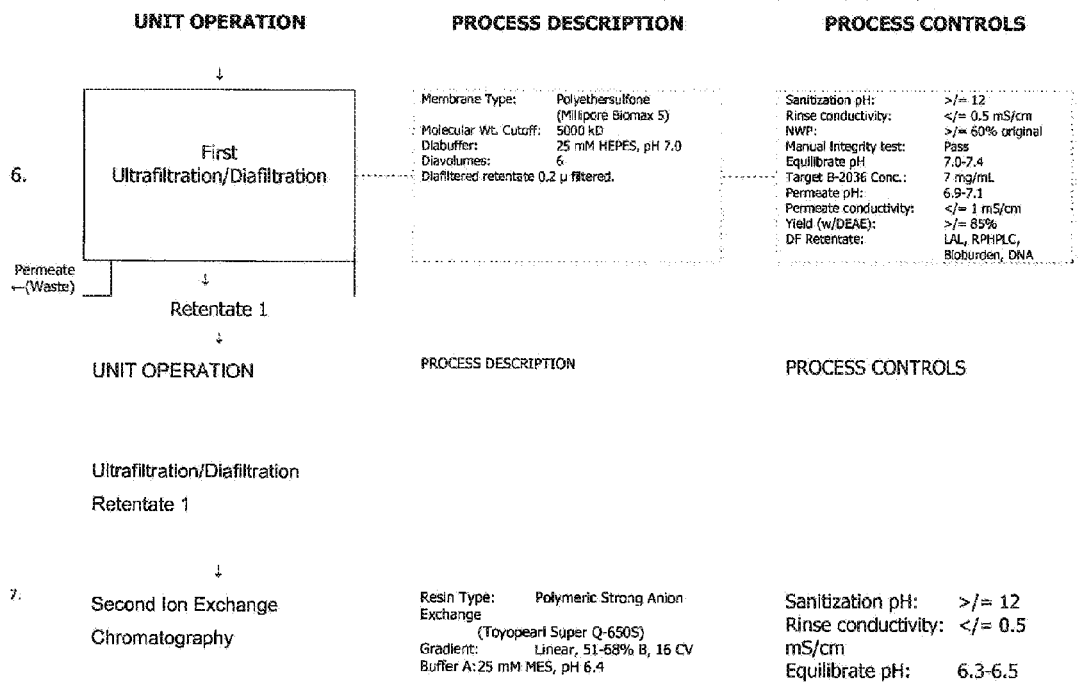
Figure 3D:
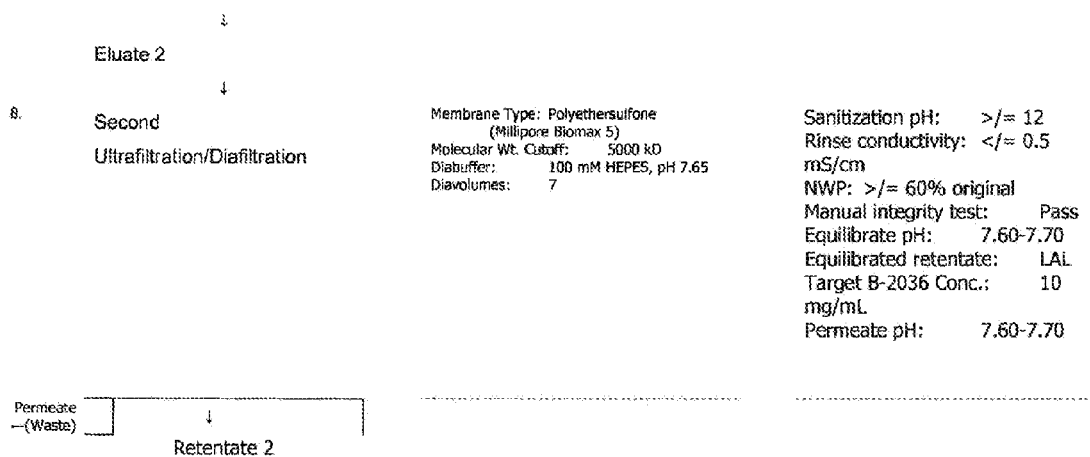

FIG. 1B illustrates the amino acid sequence structure of the trisulfide isoform impurity of B-2036. In particular, the trisulfide isoform impurity contains an extra sulfur atom in the bridge between the cysteines at positions 182 and 189 of the B-2036 protein component.

a. Decrease of Trisulfide Isoform Impurity with Mercapto Compound(s)

Without being bound by theory, it is believed that contact between selected mercapto compound(s) and the trisulfide isoform impurity of the recombinant growth hormone antagonist B-2036 results in converting the cysteine-S—S—S-cysteine trisulfide bridge back to its cysteine-S—S-cysteine native form. Additionally, also without being bound by theory, it is possible that the presence of the mercapto compound(s) prevents further formation of the trisulfide bridge itself.

Typically, the mercapto compound(s) is/are added to the host cell(s) synthesizing the desired recombinant B-2036 protein component during or after (or during and after) growth of the host cell(s). Furthermore, after the growing and contacting steps have been conducted, it is preferred to purify the B-2036 protein. Thereafter, the purified protein is preferably pegylated to yield PEG B-2036 (pegvisomant). For pegylation procedures see U.S. Pat. No. 5,849,535.

Any mercapto compound may be used in connection with the present invention which, when contacted (preferably, with adequate mixing) with the B-2036 protein component together with its trisulfide isoform impurity, is one that is sufficient to decrease the level of the trisulfide isoform impurity, preferably without degrading (or substantially degrading) the yield of B-2036. Preferred mercapto compounds suitable for use with the present invention include, but are not limited to, sulfites, glutathione, beta-mercaptoethanol, dithiothreitol, mercaptoethylamine, dithioerythritol, tris(2-carboxyethyl) phosphine hydrochloride, cysteine, and cysteine in combination with cystine.

Other suitable mercapto compounds for use with the present invention are noted in the following references: (1) J. Houk and G. M. Whitesides, "Structure-Reactivity Relations for Thiol-Disulfide Interchange," J. M. Chem. Soc., 109: 6825-6836 (1987); (2) Sigmund, M., The Chemistry & Biochemistry of the Sulfhydro Group in Amino Acids, Peptides and Proteins, $1^{st}$ Ed. Pergamon, New York (1973). In particular, see Table II of Houk et al. identified in item (1) above for a listing of exemplary mercapto compounds suitable for use with the present invention.

Of suitable mercapto compounds, cysteine, or cysteine in combination with cystine (dimerized cysteine), is most preferred. The amount of cysteine or combination of cysteine and cystine (dimerized cysteine, if any) that is suitable for use with the present invention should be that amount which is sufficient to decrease the trisulfide isoform impurity by at least about 10% of its highest equilibrium concentration (or its highest average equilibrium concentration, where multiple batches are averaged) formed. Preferably, the decrease in the amount of the trisulfide isoform impurity is least about 20%, 30%, 40%, or 50%, respectively, of its highest equilibrium concentration (or its highest average equilibrium concentration) formed. The initial combined concentration of cysteine and any cystine suitable for use with the present invention is preferably at least about 0.1 mM, from about 0.1 mM to about 10 mM, or from about 1 mM to about 5 mM, respectively.

It is preferred to provide the mercapto compound in a buffer. Preferably, the buffer is one that is suitable for use with the present invention, i.e., does not prevent the formation of the B-2036 protein component or degrade it once it is formed. Suitable buffers for use in connection with the present invention include, but are not limited to, Tris, phosphate, HEPES, citric acid, triethylamine, and histidine. The preferred buffer is Tris. The preferred initial buffer concentration is from about 1 mM to about 200 mM, more preferably from about 5 mM to about 100 mM, even more preferably from about 8 mM to about 70 mM, and most preferably from about 10 mM to about 50 mM. Other suitable buffers may be used. Preferably, these buffers are sufficient to maintain the pH of the growth medium anywhere in the range from about 4 to about 9, from about 7.5 to about 8.5, or from about 7.5 to about 8.0, respectively. Notably, where higher concentrations of mercapto compound are used, higher pH levels, for example, as high as about 9.5 may be tolerated. Thus, for example, if a large excess of cysteine to B-2036 is used, then the pH of the buffer may be as high as about 9.5.

As noted above, it is preferred to provide the mercapto compound in a buffer. Furthermore, the amount of the mercapto compound in the buffer should be such that the molar ratio of the moles of mercapto compound to the moles of B-2036 protein is from about 0.5 to about 1,000. This is especially so when the mercapto compound being used is a combination of cysteine and, optionally, cysteine in combination with cystine. Alternatively, the molar ratio of the moles of mercapto compound to the moles of B-2036 protein may be from about 1 to about 1,000, from about 1 to about 500, or from about 1 to about 10, respectively.

Typically, after sufficient contact (to decrease the level of the trisulfide isoform impurity) between the mercapto compound and the B-2036 protein component (within or from the host cell(s) has been completed), the B-2036 protein component in the buffer has a concentration from about 0.1 mg/ml to about 30 mg/ml, from about 0.5 mg/ml to about 20 mg/ml, or from about 1 mg/ml to about 10 mg/ml, respectively.

Furthermore, the temperature range of the growth medium together with the buffer, the mercapto compound(s) and its other contents including, but not limited to, B-2036, should be maintained at a temperature preferably from about 0° C. to about 25° C. after the mercapto compound has been added to the host cell(s) or lysate thereof containing the B-2036 protein component. Also, preferably, the temperature of the host cell(s) and/or lysate therefrom containing the B-2036 component is maintained from about 1° C. to about 15° C., from about 2° C. to about 10° C., or from about 2° C. to about 8° C., respectively. It is important to note that B-2036 protein denaturation occurs at about 40+° C. As such, it is desirable to maintain the temperature of the homogenate (i.e., containing host cells, growth medium, buffer, mercapto compounds and B-2036, etc.) to a temperature below the protein denaturation temperature of B-2036.

Additionally, the contact time between the B-2036 component and the mercapto compound should be for a time sufficient to decrease the level of the trisulfide isoform impurity. Exemplary suitable contact times for decreasing the level of the trisulfide isoform impurity should be for at least about 30 minutes, from about 1 hour to about 24 hours, or from about 1 hour to about 4 hours, respectively.

Typically, after sufficient contact between the mercapto compound(s) and the B-2036 component, the buffer containing the same has a volume from about 1 liter to about 5,000 liters, from about 10 liters to about 500 liters, or from 100 liters to about 300 liters, respectively. Other suitable exemplary volumes may be anywhere from 160 liters to about 500 liters.

Other parameters that may be of interest during contact between the mercapto compound(s) and the B-2036 component include things such as mixing rate. The mixing rate should be that which is sufficient to form a homogenous mixture (of the host cell(s), lysate thereof, buffer, mercapto compound(s), the B-2036 component and any other components in one growth medium) while minimizing the amount of foaming that may be formed. Those of ordinary skill can readily determine what a sufficient mixing rate should be. Obviously, the mixing rate should be such that the temperature is maintained in the above-noted ranges and any degradation of the B-2036 protein component is minimized.

b. Decrease of Trisulfide Isoform Impurity with Chelating Agent(s)

Without being bound by theory, it is believed that contact between selected chelating agent(s) and (1) the trisulfide isoform impurity, (2) the recombinant growth hormone antagonist B-2036, (3) host cell cellular component(s) (for recombinant production of the antagonist), and (4) all combinations of (1)-(3) results in converting the cysteine-S—S—S-cysteine trisulfide bridge back to its cysteine-S—S-cysteine native form or decreasing levels of the impurity. Additionally, also without being bound by theory, it is possible that the presence of the chelating agent(s) prevents further formation of the trisulfide bridge itself.

Typically, the chelating agent(s) is/are added to the host cell(s) synthesizing the desired recombinant B-2036 protein component during or after (or during and after) growth of the host cell(s). Furthermore, after the growing and contacting steps have been conducted, it is preferred to purify the B-2036 protein. Thereafter, the purified protein is preferably pegylated to yield PEG B-2036 (pegvisomant). For pegylation procedures see U.S. Pat. No. 5,849,535.

Any chelating agent may be used in connection with the present invention which, when contacted (preferably with adequate mixing) with the B-2036 protein component together with its trisulfide isoform impurity, is one that is sufficient to decrease the level of the trisulfide isoform impurity, preferably without degrading (or substantially degrading) the yield of B-2036. Preferred chelating agents suitable for use with the present invention include, but are not limited to, EDTA, EGTA, and DTPA. Additional exemplary chelating agents include, but are not limited to, Deferoxamine, Ditiocarb Sodium, Edetate Calcium Disodium, Edetate Disodium, Edetate Sodium, Edetate Trisodium, Penicillamine, Pentetate Calcium Trisodium, Pentetic Acid, Succimer, and Trientine. Note that Edetate Sodium is the salt form of EDTA.

Other suitable chelating agents for use with the present invention are noted in the following references: (1) The Merck Index, 12$^{th}$ Edition, S. Budavari (Editor), Merck & Co., Inc., Therapeutic Category and Biological Activity Index, p. THER-19 (under "CHELATING AGENT"), Whitehouse Station, N.J. (1996) and each and every subsequent edition to date thereof, (2) Remington's Pharmaceutical Sciences, 16$^{th}$ Ed., Arthur Osol (Editor), Mack Publishing Co., Easton, Pa. (1980) and each and every subsequent edition to date thereof, (3) The United States Pharmacopeia, 21$^{st}$ Revision (16$^{th}$ Edition), United States Pharmacopeial Convention, Inc., Rockville, Md. (1985) and each and every subsequent edition to date thereof, (4) SIGMA, Biochemicals and Reagents for Life Science Research Catalogue, St. Louis, Mo. (2002-2003); and (5) Aldrich, Handbook of Fine Chemicals and Laboratory Equipment, Milwaukee, Wis. (2000-2001) and (2002-2003) editions thereof.

Of suitable chelating agents, EDTA is most preferred. The amount of chelating agent that is suitable for use with the present invention should be that amount which is sufficient to decrease the trisulfide isoform impurity by at least about 10% of its highest equilibrium concentration (or its highest average equilibrium concentration, where multiple batches are averaged) formed. Preferably, the decrease in the amount of the trisulfide isoform impurity is least about 20%, 30%, 40%, or 50%, respectively, of its highest equilibrium concentration (or its highest average equilibrium concentration) formed. The initial concentration of EDTA suitable for use with the present invention is preferably at least about 0.01 mM, from about 0.01 mM to about 100 mM, from about 0.1 mM to about 20 mM, from about 2 mM to about 10 mM or from about 2 to about 5 mM, respectively.

It is preferred to provide the chelating agent in a buffer. Preferably, the buffer is one that is suitable for use with the present invention, i.e., does not prevent the formation of the B-2036 protein component or degrade it once it is formed Suitable buffers for use in connection with the present invention include, but are not limited to, Tris, phosphate, HEPES, citric acid, triethylamine, and histidine. The preferred buffer is Tris. The preferred initial buffer concentration is from about 1 mM to about 200 mM, more preferably from about 5 mM to about 100 mM, even more preferably from about 8 mM to about 70 mM, and most preferably from about 10 mM to about 50 mM. Other suitable buffers may be used. Preferably, these buffers are sufficient to maintain the pH of the growth medium anywhere in the range from about 6 to about 9, from about 6.5 to about 7.5, or from about 7.2 to about 7.5, respectively.

As noted above, it is preferred to provide the chelating agent in a buffer. Furthermore, the amount of the chelating agent in the buffer should be such that the molar ratio of the moles of chelating agent to the moles of B-2036 protein is from about 1 to about 1,000. Alternatively, the molar ratio of the moles of chelating agent to the moles of B-2036 protein may be from about 20 to about 1,000, from about 50 to about 250, or from about 60 to about 110, respectively.

Typically, after sufficient contact (to decrease the level of the trisulfide isoform impurity) between the chelating agent and the B-2036 protein component (within or from the host cell(s) has been completed), the B-2036 protein component in the buffer has a concentration from about 0.1 mg/ml to about 20 mg/ml, from about 0.5 mg/ml to about 5 mg/ml, or from about 1 mg/ml to about 5 mg/ml, respectively.

Furthermore, the temperature range of the growth medium together with the buffer, the chelating agent(s) and its other contents including, but not limited to, B-2036, should be maintained at a temperature preferably from about 0° C. to about 35° C. after the chelating agent has been added to the host cell(s) or lysate thereof containing the B-2036 protein component. Also, preferably, the temperature of the host cell(s) and/or lysate therefrom containing the B-2036 component is maintained from about 1° C. to about 15° C., from about 2° C. to about 10° C., or from about 2° C. to about 15° C., respectively. Note that, preferably, upon addition of the chelating agent (e.g., EDTA), the temperature of which is about 4° C., the temperature of the homogenate containing the B-2036 rises to about 30° C. upon homogenization. It is important to note that B-2036 protein denaturation occurs at about 40+° C. As such, it is desirable to maintain the temperature of the homogenate (i.e., containing host cells, growth medium, buffer, chelating agents, and B-2036, etc.) to a temperature below the protein denaturation temperature of B-2036.

Additionally, the contact time between the B-2036 component and the chelating agent should be for a time sufficient to decrease the level of the trisulfide isoform impurity. Exemplary suitable contact times for decreasing the level of the trisulfide isoform impurity should be for at least about 30 minutes, from about 1 hour to about 48 hours, or from about 5 hours to about 15 hours, respectively.

Typically, after sufficient contact between the chelating agent(s) and the B-2036 component, the buffer containing the same has a volume from about 1 liter to about 5,000 liters, from about 10 liters to about 500 liters, or from 100 liters to about 300 liters, respectively. Other suitable exemplary volumes may be anywhere from 160 liters to about 500 liters.

Other parameters that may be of interest during contact between the chelating agent(s) and the B-2036 component include things such as mixing rate. The mixing rate should be that which is sufficient to form a homogenous mixture (of the host cell(s), lysate thereof, buffer, chelating agent(s), the B-2036 component and any other components in the growth medium) while minimizing the amount of foaming that may be formed. Those of ordinary skill can readily determine what a sufficient mixing rate should be. Obviously, the mixing rate should be such that the temperature is maintained in the above-noted ranges and any degradation of the B-2036 protein component is minimized.

c. Decrease of Trisulfide Isoform Impurity with Metal Salt(s)

Without being bound by theory, it is believed that contact between selected metal salt(s) and (1) the trisulfide isoform impurity, (2) the recombinant growth hormone antagonist B-2036, (3) host cell cellular component(s) (for recombinant production of the antagonist), and (4) all combinations of (1)-(3) results in converting the cysteine-S—S—S-cysteine trisulfide bridge back to its cysteine-S—S-cysteine native form or decreasing levels of the impurity. Additionally, also without being bound by theory, it is possible that the presence of the metal salt(s) prevents further formation of the trisulfide bridge itself.

Typically, the metal salt(s) is/are added to the host cell(s) synthesizing the desired recombinant B-2036 protein component during or after (or during and after) growth of the host cell(s). Furthermore, after the growing and contacting steps have been conducted, it is preferred to purify the B-2036 protein. Thereafter, the purified protein is preferably pegylated to yield PEG B-2036 (pegvisomant). For pegylation procedures see U.S. Pat. No. 5,849,535.

Any metal salt may be used in connection with the present invention which, when contacted (preferably with adequate mixing) with the B-2036 protein component together with its trisulfide isoform impurity, is one that is sufficient to decrease the level of the trisulfide isoform impurity, preferably without degrading (or substantially degrading) the yield of B-2036. Metal salt(s) suitable for use with the present invention include, but are not limited to, alkali earth metal salt(s), alkaline earth metal salt(s), transition metal salt(s) and combinations thereof. Preferred metal salts suitable for use with the present invention include, but are not limited to, potassium phosphate, potassium acetate, sodium phosphate, sodium acetate, zinc chloride, and combinations thereof.

Other suitable metal salts are noted in the following references: (1) The Merck Index, $12^{th}$ Edition, S. Budavari (Editor), Merck & Co., Inc., Therapeutic Category and Biological Activity Index, p. THER-19 (under "CHELATING AGENT"), Whitehouse Station, N.J. (1996) and each and every subsequent edition to date thereof, (2) Remington's Pharmaceutical Sciences, $16^{th}$ Ed. Arthur Osol (Editor), Mack Publishing Co., Easton, Pa. (1980) and each and every subsequent edition to date thereof; (3) The United States Pharmacopeia, $21^{st}$ Revision ($16^{th}$ Edition), United States Pharmacopeial Convention, Inc., Rockville, Md. (1985) and each and every subsequent edition to date thereof, (4) SIGMA, Biochemicals and Reagents for Life Science Research Catalogue, St. Louis, Mo. (2002-2003); and (5) Aldrich, Handbook of Fine Chemicals and Laboratory Equipment, Milwaukee, Wis. (2000-2001) and (2002-2003) editions thereof.

Of suitable metal salts for use with the present invention sodium phosphate, $ZnCl_2$ and combinations thereof are also preferred. The amount of metal salt(s) suitable for use with the present invention should be that amount which is sufficient to decrease the trisulfide isoform impurity by at least about 10% of its highest concentration (or its highest average concentration, where multiple batches are averaged) formed. Preferably, the decrease in the amount of the trisulfide isoform impurity is least about 20%, 30%, 40%, or 50%, respectively, of its highest concentration (or its highest average concentration) formed. The initial concentration of metal salt (e.g., sodium phosphate) suitable for use with the present invention is preferably at least about 0.1 mM, from about 1 mM to about 500 mM, from about 1 mM to about 200 mM, from about 5 mM to about 175 mM, from about 10 mM to about 150 mM or from about 25 to about 100 mM, respectively.

It is preferred to provide the metal salt in a buffer. However, sodium phosphate can act both as a buffer and a suitable metal salt. However, additional suitable metal salt(s) may be added to the sodium phosphate buffer. Preferably, the buffer is one that is suitable for use with the present invention, i.e., does not prevent the formation of the B-2036 protein component or degrade it once it is formed Suitable buffers for use in connection with the present invention include, but are not limited to, Tris, phosphate, HEPES, citric acid, triethylamine, and histidine. The preferred initial buffer concentration is from about 1 mM to about 200 mM, more preferably from about 5 mM to about 100 mM, even more preferably from about 8 mM to about 70 mM and most preferably from about 10 mM to about 50 mM. Other suitable buffers may be used. Preferably, these buffers are sufficient to maintain the pH of the growth medium anywhere in the range from about 4 to about 9, from about 4.5 to about 7.5, or from about 5.5 to about 7.5, respectively.

After the metal salt is provided in a buffer (or in the case of NaP, where the NaP solution acts both as the metal salt and the buffer), the amount of the metal salt in the buffer (or NaP solution also acting as the buffer) should be such that the molar ratio of the moles of metal salt to the moles of B-2036 protein is from about 1 to about 10,000. Alternatively, the molar ratio of the moles of the metal salt to the moles of B-2036 protein may be from about 300 to about 10,000, from about 500 to about 5,000, or from about 500 to about 2500, respectively.

Typically, after sufficient contact (to decrease the level of the trisulfide isoform impurity) between the metal salt(s) and the B-2036 protein component (within or from the host cell(s) has been completed), the B-2036 protein component in the buffer has a concentration from about 0.1 mg/ml to about 20 mg/ml, from about 0.5 mg/ml to about 5 mg/ml, or from about 1 mg/ml to about 5 mg/ml, respectively.

Furthermore, the temperature range of the growth medium together with the buffer, the metal salt(s) and its other contents including, but not limited to, B-2036, preferably should be maintained at a temperature from about 0° C. to about 35° C. after the metal salt has been added to the host cell(s) or lysate thereof containing the B-2036 protein component. Also, preferably, the temperature of the host cell(s) and/or lysate therefrom containing the B-2036 component is maintained from about 1° C. to about 15° C., from about 2° C. to about 10° C., or from about 2° C. to about 15° C., respectively. Note that upon homogenization with the metal salt (e.g., NaP), the temperature of the homogenate may rise. It is important to note that B-2036 protein denaturation occurs at about 40+° C. As such, it is desirable to maintain the temperature of the homogenate (i.e., containing host cells, growth medium, buffer, metal salt, B-2036, and optionally mercapto compound, etc.) to a temperature below the protein denaturation temperature of B-2036.

Additionally, the contact time between the B-2036 component and the chelating agent should be for a time sufficient to decrease the level of the trisulfide isoform impurity. Exemplary suitable contact times for decreasing the level of the trisulfide isoform impurity should be for at least about 30 minutes, from about 1 hour to about 48 hours, or from about 5 hours to about 15 hours, respectively.

Typically, after sufficient contact between the metal salt(s) and the B-2036 component, the buffer containing the same has a volume from about 1 liter to about 5,000 liters, from about 100 liters to about 2,000 liters, or from 200 liters to about 1,500 liters, respectively.

Other parameters that may be of interest during contact between the metal salt(s) and the B-2036 component include things such as mixing rate. The mixing rate should be that which is sufficient to form a homogenous mixture (of the host cell(s), lysate thereof, buffer, metal salt(s), the B-2036 component and any other components in the growth medium) while minimizing the amount of foaming that may be formed. Those of ordinary skill can readily determine what a sufficient mixing rate should be. Obviously, the mixing rate should be such that the temperature is maintained in the above-noted ranges and any degradation of the B-2036 protein component is minimized.

2. Recombinant Growth Hormone Antagonist and its Des-Phe Isoform Impurity a. Decrease of Des-Phe Isoform Impurity with Chelating Agent Without being bound by theory, it is believed that addition of chelating agent(s) to the recombinant growth hormone antagonist B-2036 results in a decrease in the level of the des-phe isoform impurity either by an actual reduction in the level thereof and/or prevention of further des-phe formation.

Typically, the chelating agent(s) is/are added to the host cell(s) synthesizing the desired recombinant B-2036 protein component during or after (or during and after) growth of the host cell(s). Furthermore, after the growing and contacting steps have been conducted, it is preferred to purify the B-2036 protein. Thereafter, the purified protein is preferably pegylated to yield PEG B-2036 (pegvisomant). For pegylation procedures see U.S. Pat. No. 5,849,535.

Any chelating agent may be used in connection with the present invention which, when contacted (preferably with adequate mixing) with the B-2036 protein component together with its des-phe isoform impurity, is one that is sufficient to decrease the level of the des-phe isoform impurity, preferably without degrading (or substantially degrading) the yield of B-2036. Preferred chelating agents suitable for use with the present invention include, but are not limited to, EDTA, EGTA, and DTPA. Additional exemplary chelating agents include, but are not limited to, Deferoxamine, Ditiocarb Sodium, Edetate Calcium Disodium, Edetate Disodium, Edetate Sodium, Edetate Trisodium, Penicillamine, Pentetate Calcium Trisodium, Pentetic Acid, Succimer, and Trientine. Note that Edetate Sodium is the salt form of EDTA.

Other suitable chelating agents for use with the present invention are noted in the following references: (1) The Merck Index, 12$^{th}$ Edition, S. Budavari (Editor), Merck & Co., Inc., Therapeutic Category and Biological Activity Index, p. THER-19 (under "CHELATING AGENT"), Whitehouse Station, N.J. (1996) and each and every subsequent edition to date thereof, (2) Remington's Pharmaceutical Sciences, 16$^{th}$ Ed., Arthur Osol (Editor), Mack Publishing Co., Easton, Pa. (1980) and each and every subsequent edition to date thereof, (3) The United States Pharmacopeia, 21$^{st}$ Revision (16$^{th}$ Edition), United States Pharmacopeial Convention, Inc., Rockville, Md. (1985) and each and every subsequent edition to date thereof, (4) SIGMA, Biochemicals and Reagents for Life Science Research Catalogue, St. Louis, Mo. (2002-2003); and (5) Aldrich, Handbook of Fine Chemicals and Laboratory Equipment, Milwaukee, Wis. (2000-2001) and (2002-2003) editions thereof.

Of suitable chelating agents, EDTA is most preferred. The amount of chelating agent that is suitable for use with the present invention should be that amount which is sufficient to decrease the des-phe isoform impurity by at least about 10% of its highest equilibrium concentration (or its highest average equilibrium concentration, where multiple batches are averaged) formed. Preferably, the decrease in the amount of the des-phe isoform impurity is least about 20%, 30%, 40%, or 50%, respectively, of its highest equilibrium concentration (or its highest average equilibrium concentration) formed. The initial concentration of EDTA suitable for use with the present invention is preferably at least about 0.01 mM, from about 0.01 mM to about 100 mM, from about 0.1 mM to about 20 mM, from about 2 mM to about 10 mM or from about 2 to about 5 mM, respectively.

It is preferred to provide the chelating agent in a buffer. Preferably, the buffer is one that is suitable for use with the present invention, i.e., does not prevent the formation of the B-2036 protein component or degrade it once it is formed Suitable buffers for use in connection with the present invention include, but are not limited to, Tris, phosphate, HEPES, citric acid, triethylamine, and histidine. The preferred buffer is Tris. The preferred initial buffer concentration is from about 1 mM to about 200 mM, more preferably from about 5 mM to about 100 mM, even more preferably from about 8 mM to about 70 mM, and most preferably from about 10 mM to about 50 mM. Other suitable buffers may be used. Preferably, these buffers are sufficient to maintain the pH of the growth medium anywhere in the range from about 6 to about 9, from about 6.5 to about 7.5, or from about 7.2 to about 7.5, respectively.

As noted above, it is preferred to provide the chelating agent in a buffer. Furthermore, the amount of the chelating agent in the buffer should be such that the molar ratio of the moles of chelating agent to the moles of B-2036 protein is from about 1 to about 1,000. Alternatively, the molar ratio of the moles of chelating agent to the moles of B-2036 protein may be from about 20 to about 1,000, from about 50 to about 250, or from about 60 to about 110, respectively.

Typically, after sufficient contact (to decrease the level of the des-phe isoform impurity) between the chelating agent and the B-2036 protein component (within or from the host cell(s) has been completed), the B-2036 protein component in the buffer has a concentration from about 0.1 mg/ml to about 20 mg/ml, from about 0.5 mg/ml to about 5 mg/ml, or from about 1 mg/ml to about 5 mg/ml, respectively.

Furthermore, the temperature range of the growth medium together with the buffer, the chelating agent(s) and its other contents including, but not limited to, B-2036, should be maintained at a temperature preferably from about 0° C. to about 35° C. after the chelating agent has been added to the host cell(s) or lysate thereof containing the B-2036 protein component. Also, preferably, the temperature of the host cell(s) and/or lysate therefrom containing the B-2036 component is maintained from about 1° C. to about 15° C., from about 2° C. to about 10° C., or from about 2° C. to about 15° C., respectively. Note that, preferably, upon addition of the chelating agent (e.g., EDTA), the temperature of which is about 4° C., the temperature of the homogenate containing the B-2036 rises to about 30° C. upon homogenization. It is important to note that B-2036 protein denaturation occurs at about 40+° C. As such, it is desirable to maintain the temperature of the homogenate (i.e., containing host cells, growth medium, buffer, chelating agents, and B-2036, etc.) to a temperature below the protein denaturation temperature of B-2036.

Additionally, the contact time between the B-2036 component and the chelating agent should be for a time sufficient to decrease the level of the des-phe isoform impurity. Exemplary suitable contact times for decreasing the level of the des-phe isoform impurity should be for at least about 30 minutes, from about 1 hour to about 48 hours, or from about 5 hours to about 15 hours, respectively.

Typically, after sufficient contact between the chelating agent(s) and the B-2036 component, the buffer containing the same has a volume from about 1 liter to about 5,000 liters, from about 10 liters to about 500 liters, or from 100 liters to about 300 liters, respectively. Other suitable exemplary volumes may be anywhere from 160 liters to about 500 liters.

Other parameters that may be of interest during contact between the chelating agent(s) and the B-2036 component include things such as mixing rate. The mixing rate should be that which is sufficient to form a homogenous mixture (of the host cell(s), lysate thereof, buffer, chelating agent(s), the B-2036 component and any other components in the growth medium) while minimizing the amount of foaming that may be formed. Those of ordinary skill can readily determine what a sufficient mixing rate should be. Obviously, the mixing rate should be such that the temperature is maintained in the above-noted ranges and any degradation of the B-2036 protein component is minimized.

b. Decrease of Des Phe Isoform Impurity with Metal Salt

Without being bound by theory, it is believed that addition of metal salt(s) to the recombinant growth hormone antagonist B-2036 results in a decrease in the level of the des-phe isoform impurity either by an actual reduction in the level thereof and/or prevention of further des-phe formation.

Typically, the metal salt(s) is/are added to the host cell(s) synthesizing the desired recombinant B-2036 protein component during or after (or during and after) growth of the host cell(s). Furthermore, after the growing and contacting steps have been conducted, it is preferred to purify the B-2036 protein. Thereafter, the purified protein is preferably pegylated to yield PEG B-2036 (pegvisomant). For pegylation procedures see U.S. Pat. No. 5,849,535.

Any metal salt may be used in connection with the present invention which, when contacted (preferably with adequate mixing) with the B-2036 protein component together with its des-phe isoform impurity, is one that is sufficient to decrease the level of the des-phe isoform impurity, preferably without degrading (or substantially degrading) the yield of B-2036. Metal salt(s) suitable for use with the present invention include, but are not limited to, alkali earth metal salt(s), alkaline earth metal salt(s), transition metal salt(s) and combinations thereof. Preferred metal salts suitable for use with the present invention include, but are not limited to, potassium phosphate, potassium acetate, sodium phosphate, sodium acetate, zinc chloride, and combinations thereof.

Other suitable metal salts for use with the present invention are noted in the following references: (1) The Merck Index, 12$^{th}$ Edition, S. Budavari (Editor), Merck & Co., Inc., Therapeutic Category and Biological Activity Index, p. THER-19 (under "CHELATING AGENT"), Whitehouse Station, N.J. (1996) and each and every subsequent edition to date thereof, (2) Remington's Pharmaceutical Sciences, 16$^{th}$ Ed. Arthur Osol (Editor), Mack Publishing Co., Easton, Pa. (1980) and each and every subsequent edition to date thereof, (3) The United States Pharmacopeia, 21$^{st}$ Revision (16$^{th}$ Edition), United States Pharmacopeial Convention, Inc., Rockville, Md. (1985) and each and every subsequent edition to date thereof, (4) SIGMA, Biochemicals and Reagents for Life Science Research Catalogue, St. Louis, Mo. (2002-2003); and (5) Aldrich, Handbook of Fine Chemicals and Laboratory Equipment, Milwaukee, Wis. (2000-2001) and (2002-2003) editions thereof.

Of suitable metal salts for use with the present invention sodium phosphate, $ZnCl_2$ and combinations thereof are also preferred. The amount of metal salt(s) suitable for use with the present invention should be that amount which is sufficient to decrease the des-phe isoform impurity by at least about 10% of its highest concentration (or its highest average concentration, where multiple batches are averaged) formed. Preferably, the decrease in the amount of the des-phe isoform impurity is least about 20%, 30%, 40%, or 50%, respectively, of its highest concentration (or its highest average concentration) formed. The initial concentration of metal salt (e.g., sodium phosphate) suitable for use with the present invention is preferably at least about 0.1 mM, from about 1 mM to about 500 mM, from about 1 mM to about 200 mM, from about 5 mM to about 175 mM, from about 10 mM to about 150 mM or from about 25 to about 100 mM, respectively.

It is preferred to provide the metal salt in a buffer. However, sodium phosphate can act both as a buffer and a suitable metal salt. However, additional suitable metal salt(s) may be added to the sodium phosphate buffer. Preferably, the buffer is one that is suitable for use with the present invention, i.e., does not degrade the formation of the B-2036 protein component. Suitable buffers for use in connection with the present invention include, but are not limited to, Tris, phosphate, HEPES, citric acid, triethylamine, and histidine. The preferred initial buffer concentration is from about 1 mM to about 200 mM, more preferably from about 5 mM to about 100 mM, even more preferably from about 8 mM to about 70 mM and most preferably from about 10 mM to about 50 mM. Other suitable buffers may be used. Preferably, these buffers are sufficient to maintain the pH of the growth medium anywhere in the range from about 4 to about 9, from about 4.5 to about 7.5, or from about 5.5 to about 7.5, respectively.

After the metal salt is provided in a buffer (or in the case of NaP, where the NaP solution acts both as the metal salt and the buffer), the amount of the metal salt in the buffer (or NaP solution also acting as the buffer) should be such that the molar ratio of the moles of metal salt to the moles of B-2036 protein is from about 1 to about 10,000. Alternatively, the molar ratio of the moles of the metal salt to the moles of B-2036 protein may be from about 300 to about 10,000, from about 500 to about 5,000, or from about 500 to about 2500, respectively.

Typically, after sufficient contact (to decrease the level of the des-phe isoform impurity) between the metal salt(s) and the B-2036 protein component (within or from the host cell(s) has been completed), the B-2036 protein component in the buffer has a concentration from about 0.1 mg/ml to about 20 mg/ml, from about 0.5 mg/ml to about 5 mg/ml, or from about 1 mg/ml to about 5 mg/ml, respectively.

Furthermore, the temperature range of the growth medium together with the buffer, the metal salt(s) and its other contents including, but not limited to, B-2036, preferably should be maintained at a temperature from about 0° C. to about 35° C. after the metal salt has been added to the host cell(s) or lysate thereof containing the B-2036 protein component. Also preferably, the temperature of the host cell(s) and/or lysate therefrom containing the B-2036 component is maintained from about 1° C. to about 15° C., from about 2° C. to about 10° C., or from about 2° C. to about 15° C., respectively. Note that upon homogenization with the metal salt (e.g., NaP), the temperature of the homogenate may rise. It is important to note that B-2036 protein denaturation occurs at about 40+° C. As such, it is desirable to maintain the temperature of the homogenate (i.e., containing host cells, growth medium, buffer, metal salt, B-2036, and optionally mercapto compound, etc.) to a temperature below the protein denaturation temperature of B-2036.

Additionally, the contact time between the B-2036 component and the metal salt should be for a time sufficient to decrease the level of the des-phe isoform impurity. Exemplary suitable contact times for decreasing the level of the des-phe isoform impurity should be for at least about 30 minutes, from about 1 hour to about 48 hours, or from about 5 hours to about 15 hours, respectively.

Typically, after sufficient contact between the metal salt(s) and the B-2036 component, the buffer containing the same has a volume from about 1 liter to about 5,000 liters, from about 100 liters to about 2,000 liters, or from 200 liters to about 1,500 liters, respectively.

Other parameters that may be of interest during contact between the metal salt(s) and the B-2036 component include things such as mixing rate. The mixing rate should be that which is sufficient to form a homogenous mixture (of the host cell(s), lysate thereof, buffer, metal salt(s), the B-2036 component and any other components in the growth medium) while minimizing the amount of foaming that may be formed. Those of ordinary skill can readily determine what a sufficient mixing rate should be. Obviously, the mixing rate should be such that the temperature is maintained in the above-noted ranges and any degradation of the B-2036 protein component is minimized.

3. Recombinant Growth Hormone and its Des-Phe Isoform Impurity a. Decrease of Des-Phe Isoform Impurity with Chelating Agent Without being bound by theory, it is believed that addition of chelating agent(s) to the recombinant growth hormone results in a decrease in the level of the des-phe isoform impurity either by an actual reduction in the level thereof and/or prevention of further des-phe formation.

Typically, the chelating agent(s) is/are added to the host cell(s) synthesizing the desired recombinant growth hormone protein during or after (or during and after) growth of the host cell(s). Furthermore, after the growing and contacting steps have been conducted, it is preferred to purify the growth hormone protein.

Any chelating agent may be used in connection with the present invention which, when contacted (preferably with adequate mixing) with the growth hormone protein together with its des-phe isoform impurity, is one that is sufficient to decrease the level of the des-phe isoform impurity, preferably without degrading (or substantially degrading) the yield of the growth hormone. Preferred chelating agents suitable for use with the present invention include, but are not limited to, EDTA, EGTA, and DTPA. Additional exemplary chelating agents include, but are not limited to, Deferoxamine, Ditiocarb Sodium, Edetate Calcium Disodium, Edetate Disodium, Edetate Sodium, Edetate Trisodium, Penicillamine, Pentetate Calcium Trisodium, Pentetic Acid, Succimer, and Trientine. Note that Edetate Sodium is the salt form of EDTA.

Other suitable chelating agents for use with the present invention are noted in the following references: (1) The Merck Index, 12$^{th}$ Edition, S. Budavari (Editor), Merck & Co., Inc., Therapeutic Category and Biological Activity Index, p. THER-19 (under "CHELATING AGENT"), Whitehouse Station, N.J. (1996) and each and every subsequent edition to date thereof, (2) Remington's Pharmaceutical Sciences, 16$^{th}$ Ed., Arthur Osol (Editor), Mack Publishing Co., Easton, Pa. (1980) and each and every subsequent edition to date thereof, (3) The United States Pharmacopeia, 21$^{st}$ Revision (16$^{th}$ Edition), United States Pharmacopeial Convention, Inc., Rockville, Md. (1985) and each and every subsequent edition to date thereof, (4) SIGMA, Biochemicals and Reagents for Life Science Research Catalogue, St. Louis, Mo. (2002-2003); and (5) Aldrich, Handbook of Fine Chemicals and Laboratory Equipment, Milwaukee, Wis. (2000-2001) and (2002-2003) editions thereof.

Of suitable chelating agents, EDTA is most preferred. The amount of chelating agent that is suitable for use with the present invention should be that amount which is sufficient to decrease the des-phe isoform impurity by at least about 10% of its highest equilibrium concentration (or its highest average equilibrium concentration, where multiple batches are averaged) formed. Preferably, the decrease in the amount of the des-phe isoform impurity is least about 20%, 30%, 40%, or 50%, respectively, of its highest equilibrium concentration (or its highest average equilibrium concentration) formed. The initial concentration of EDTA suitable for use with the present invention is preferably at least about 0.01 mM, from about 0.01 mM to about 100 mM, from about 0.1 mM to about 20 mM, from about 2 mM to about 10 mM or from about 2 to about 5 mM, respectively.

It is preferred to provide the chelating agent in a buffer. Preferably, the buffer is one that is suitable for use with the present invention, i.e., does not prevent the formation of the B-2036 protein component or degrade it once it is formed. Suitable buffers for use in connection with the present invention include, but are not limited to, Tris, phosphate, HEPES, citric acid, triethylamine, and histidine. The preferred buffer is Tris. The preferred initial buffer concentration is from about 1 mM to about 200 mM, more preferably from about 5 mM to about 100 mM, even more preferably from about 8 mM to about 70 mM, and most preferably from about 10 mM to about 50 mM. Other suitable buffers may be used. Preferably, these buffers are sufficient to maintain the pH of the growth medium anywhere in the range from about 6 to about 9, from about 6.5 to about 7.5, or from about 7.2 to about 7.5, respectively.

As noted above, it is preferred to provide the chelating agent in a buffer. Furthermore, the amount of the chelating agent in the buffer should be such that the molar ratio of the moles of chelating agent to the moles of growth hormone protein (e.g., hGH) is from about 1 to about 1,000. Alternatively, the molar ratio of the moles of chelating agent to the moles of growth hormone protein (e.g., hGH) may be from about 20 to about 1,000, from about 50 to about 250, or from about 60 to about 110, respectively.

Typically, after sufficient contact (to decrease the level of the des-phe isoform impurity) between the chelating agent and the growth hormone protein (e.g., hGH) (within or from the host cell(s) has been completed), the growth hormone protein (e.g., hGH) in the buffer has a concentration from about 0.1 mg/ml to about 20 mg/ml, from about 0.5 mg/ml to about 5 mg/ml, or from about 1 mg/ml to about 5 mg/ml, respectively.

Furthermore, the temperature range of the growth medium together with the buffer, the chelating agent(s) and its other contents including, but not limited to, the growth hormone protein, preferably should be maintained at a temperature preferably from about 0° C. to about 35° C. after the chelating agent has been added to the host cell(s) or lysate thereof containing the growth hormone protein. Also, preferably, the temperature of the host cell(s) and/or lysate therefrom containing the growth hormone protein is maintained from about 1° C. to about 15° C., from about 2° C. to about 10° C., or from about 2° C. to about 15° C., respectively. Note that, preferably, upon addition of the chelating agent (e.g., EDTA), the temperature of which is about 4° C., the temperature of the homogenate containing the growth hormone rises to about 30° C. upon homogenization. It is important to note that growth hormone protein denaturation occurs at about 40+° C. As such, it is desirable to maintain the temperature of the homogenate (i.e., containing host cells, growth medium, buffer, chelating agents, and growth hormone protein, etc.) to a temperature below the protein denaturation temperature of growth hormone protein.

Additionally, the contact time between the growth hormone protein and the chelating agent should be for a time sufficient to decrease the level of the des-phe isoform impurity. Exemplary suitable contact times for decreasing the level of the des-phe isoform impurity should be for at least about 30 minutes, from about 1 hour to about 48 hours, or from about 5 hours to about 15 hours, respectively.

Typically, after sufficient contact between the chelating agent(s) and the growth hormone protein, the buffer containing the same has a volume from about 1 liter to about 5,000 liters, from about 10 liters to about 500 liters, or from 100 liters to about 300 liters, respectively. Other suitable exemplary volumes may be anywhere from 160 liters to about 500 liters.

Other parameters that may be of interest during contact between the chelating agent(s) and the growth hormone protein include things such as mixing rate. The mixing rate should be that which is sufficient to form a homogenous mixture (of the host cell(s), lysate thereof, buffer, chelating agent(s), the growth hormone protein and any other components in the growth medium) while minimizing the amount of foaming that may be formed. Those of ordinary skill can readily determine what a sufficient mixing rate should be. Obviously, the mixing rate should be such that the temperature is maintained in the above-noted ranges and any degradation of the growth hormone protein component is minimized.

b. Decrease of Des-Phe Isoform Impurity with Metal Salt

Without being bound by theory, it is believed that addition of metal salt(s) to the recombinant growth hormone results in a decrease in the level of the des-phe isoform impurity either by an actual reduction in the level thereof and/or prevention of further des-phe formation.

Typically, the metal salt(s) is/are added to the host cell(s) synthesizing the desired recombinant growth hormone protein component during or after (or during and after) growth of the host cell(s). Furthermore, after the growing and contacting steps have been conducted, it is preferred to purify the growth hormone protein.

Any metal salt may be used in connection with the present invention which, when contacted (preferably with adequate mixing) with the growth hormone protein component together with its des-phe isoform impurity, is one that is sufficient to decrease the level of the des-phe isoform impurity, preferably without degrading (or substantially degrading) the yield of growth hormone. Metal salt(s) suitable for use with the present invention include, but are not limited to, alkali earth metal salt(s), alkaline earth metal salt(s), transition metal salt(s) and combinations thereof. Preferred metal salts suitable for use with the present invention include, but are not limited to, potassium phosphate, potassium acetate, sodium phosphate, sodium acetate, zinc chloride, and combinations thereof.

Other suitable metal salts for use with the present invention are noted in the following references: (1) The Merck Index, 12$^{th}$ Edition, S. Budavari (Editor), Merck & Co., Inc., Therapeutic Category and Biological Activity Index, p. THER-19 (under "CHELATING AGENT"), Whitehouse Station, N.J. (1996) and each and every subsequent edition to date thereof, (2) Remington's Pharmaceutical Sciences, 16$^{th}$ Ed. Arthur Osol (Editor), Mack Publishing Co., Easton, Pa. (1980) and each and every subsequent edition to date thereof, (3) The United States Pharmacopeia, 21$^{st}$ Revision (16$^{th}$ Edition), United States Pharmacopeial Convention, Inc., Rockville, Md. (1985) and each and every subsequent edition to date thereof, (4) SIGMA, Biochemicals and Reagents for Life Science Research Catalogue, St. Louis, Mo. (2002-2003); and (5) Aldrich, Handbook of Fine Chemicals and Laboratory Equipment, Milwaukee, Wis. (2000-2001) and (2002-2003) editions thereof.

Of suitable metal salts for use with the present invention sodium phosphate, $ZnCl_2$ and combinations thereof are also preferred. The amount of metal salt(s) suitable for use with the present invention should be that amount which is sufficient to decrease the des-phe isoform impurity by at least about 10% of its highest concentration (or its highest average concentration, where multiple batches are averaged) formed. Preferably, the decrease in the amount of the des-phe isoform impurity is least about 20%, 30%, 40%, or 50%, respectively, of its highest concentration (or its highest average concentration) formed. The initial concentration of metal salt (e.g., sodium phosphate) suitable for use with the present invention is preferably at least about 0.1 mM, from about 1 mM to about 500 mM, from about 1 mM to about 200 mM, from about 5 mM to about 175 mM, from about 10 mM to about 150 mM or from about 25 to about 100 mM, respectively.

It is preferred to provide the metal salt in a buffer. However, sodium phosphate can act both as a buffer and a suitable metal salt. However, additional suitable metal salt(s) may be added to the sodium phosphate buffer. Preferably, the buffer is one that is suitable for use with the present invention, i.e., does not prevent the formation of the B-2036 protein component or degrade it once it is formed Suitable buffers for use in connection with the present invention include, but are not limited to, Tris, phosphate, HEPES, citric acid, triethylamine, and histidine. The preferred initial buffer concentration is from about 1 mM to about 200 mM, more preferably from about 5 mM to about 100 mM, even more preferably from about 8 mM to about 70 mM and most preferably from about 10 mM to about 50 mM. Other suitable buffers may be used. Preferably, these buffers are sufficient to maintain the pH of the growth medium anywhere in the range from about 4 to about 9, from about 4.5 to about 7.5, or from about 5.5 to about 7.5, respectively.

After the metal salt is provided in a buffer (or in the case of NaP, where the NaP solution acts both as the metal salt and the buffer), the amount of the metal salt in the buffer (or NaP solution also acting as the buffer) should be such that the molar ratio of the moles of metal salt to the moles of growth hormone protein (e.g., hGH) is from about 1 to about 10,000. Alternatively, the molar ratio of the moles of the metal salt to the moles of growth hormone protein (e.g., hGH) may be from about 300 to about 10,000, from about 500 to about 5,000, or from about 500 to about 2500, respectively.

Typically, after sufficient contact (to decrease the level of the des-phe isoform impurity) between the metal salt(s) and the growth hormone protein (e.g., hGH) (within or from the host cell(s) has been completed), the growth hormone protein in the buffer has a concentration from about 0.1 mg/ml to about 20 mg/ml, from about 0.5 mg/ml to about 5 mg/ml, or from about 1 mg/ml to about 5 mg/ml, respectively.

Furthermore, the temperature range of the growth medium together with the buffer, the metal salt(s) and its other contents including, but not limited to, the growth hormone protein, preferably should be maintained at a temperature from about 0° C. to about 35° C. after the metal salt has been added to the host cell(s) or lysate thereof containing the growth hormone protein. Also, preferably, the temperature of the host cell(s) and/or lysate therefrom containing the growth hormone protein is maintained from about 1° C. to about 15° C., from about 2° C. to about 10° C., or from about 2° C. to about 15° C., respectively. Note that upon homogenization with the metal salt (e.g., NaP), the temperature of the homogenate may rise. It is important to note that growth hormone protein denaturation occurs at about 40+° C. As such, it is desirable to maintain the temperature of the homogenate (i.e., containing host cells, growth medium, buffer, metal salt, growth hormone protein, and optionally mercapto compound, etc.) to a temperature below the protein denaturation temperature of growth hormone protein.

Additionally, the contact time between the growth hormone protein and the metal salt should be for a time sufficient to decrease the level of the des-phe isoform impurity. Exemplary suitable contact times for decreasing the level of the des-phe isoform impurity should be for at least about 30 minutes, from about 1 hour to about 48 hours, or from about 5 hours to about 15 hours, respectively.

Typically, after sufficient contact between the metal salt(s) and the growth hormone protein, the buffer containing the same has a volume from about 1 liter to about 5,000 liters, from about 100 liters to about 2,000 liters, or from 200 liters to about 1,500 liters, respectively.

Other parameters that may be of interest during contact between the metal salt(s) and the growth hormone protein include things such as mixing rate. The mixing rate should be that which is sufficient to form a homogenous mixture (of the host cell(s), lysate thereof, buffer, metal salt(s), the growth hormone protein and any other components in the growth medium) while minimizing the amount of foaming that may be formed. Those of ordinary skill can readily determine what a sufficient mixing rate should be. Obviously, the mixing rate should be such that the temperature is maintained in the above-noted ranges and any degradation of the growth hormone protein component is minimized.

EMBODIMENTS OF THE INVENTION

1. A process for decreasing the amount of an impurity produced in recombinant production of a growth hormone antagonist polypeptide in genetically modified host cells, the process comprising the step of:
   (a) contacting with said impurity under sufficient conditions a mercapto compound to decrease said amount of said impurity,
   wherein said impurity is a trisulfide isoform of said polypeptide.
2. The process of embodiment 1 further comprising the step of:
   (b) growing said host cells to produce said polypeptide, wherein said growing is conducted either before or during said contacting step (a).
3. The process of embodiment 2 further comprising the step of:
   (c) purifying said polypeptide to yield a purified polypeptide.
4. The process of embodiment 3 further comprising the step of:
   (d) pegylating said purified polypeptide.
5. The process of embodiment 2 wherein said mercapto compound is selected from the group consisting of sulfites, glutathione, beta-mercaptoethanol, dithiothreitol, mercaptoethylamine, dithioerythritol, tris(2-carboxyethyl) phosphine hydrochloride, cysteine, and cysteine in combination with cystine.
6. The process of embodiment 1 wherein said mercapto compound is selected from the group consisting of sulfites, glutathione, beta-mercaptoethanol, dithiothreitol, mercaptoethylamine, dithioerythritol, tris(2-carboxyethyl) phosphine hydrochloride, cysteine, and cysteine in combination with cystine.
7. The process of embodiment 5 wherein said mercapto compound comprises cysteine or a combination of cysteine and cystine.
8. The process of embodiment 6 wherein said mercapto compound comprises cysteine or a combination of cysteine and cystine.
9. The process of embodiment 7 wherein in said contacting step (a), said trisulfide isoform is contacted with said cysteine or combination of cysteine and cystine for a period of time sufficient to decrease said amount of said trisulfide isoform by at least about 10%.
10. The process of embodiment 9 wherein said period of time is sufficient to decrease said amount of said trisulfide isoform by at least about 50%.
11. The process of embodiment 8 wherein in said contacting step (a), said trisulfide isoform is contacted with said cysteine for a period of time sufficient to decrease said amount of said trisulfide isoform by at least about 10%.
12. The process of embodiment 11 wherein said period of time is sufficient to decrease said amount of said trisulfide isoform by at least about 50%.
13. The process of embodiment 1 wherein said mercapto compound is provided in a buffer.
14. The process of embodiment 2 wherein said mercapto compound is provided in a buffer.
15. The process of embodiment 7 wherein said cysteine or combination of cysteine and cystine is provided in a buffer.
16. The process of embodiment 8 wherein said cysteine or combination of cysteine and cystine is provided in a buffer.
17. The process of embodiment 15 wherein before said contacting step (a), said buffer has an initial combined cysteine and cystine concentration of at least about 0.1 mM.
18. The process of embodiment 16 wherein before said contacting step (a), said buffer has an initial combined cysteine and cystine concentration of at least about 0.1 mM.
19. The process of embodiment 17 wherein said initial combined cysteine and cystine concentration is from about 0.1 mM to about 10 mM.
20. The process of embodiment 18 wherein said initial combined cysteine and cystine concentration is from about 0.1 mM to about 10 mM.
21. The process of embodiment 19 wherein said initial combined cysteine and cystine concentration is from about 1 mM to about 5 mM.
22. The process of embodiment 20 wherein said initial combined cysteine and cystine concentration is from about 1 mM to about 5 mM.
23. The process of embodiment 13 wherein said buffer is selected from the group consisting of Tris, phosphate, HEPES, citric acid, triethylamine, and histidine.
24. The process of embodiment 14 wherein said buffer is selected from the group consisting of Tris, phosphate, HEPES, citric acid, triethylamine, and histidine.
25. The process of embodiment 15 wherein said buffer is selected from the group consisting of Tris, phosphate, HEPES, citric acid, triethylamine, and histidine.
26. The process of embodiment 16 wherein said buffer is selected from the group consisting of Tris, phosphate, HEPES, citric acid, triethylamine, and histidine.
27. The process of embodiment 23 wherein said buffer comprises Tris.
28. The process of embodiment 26 wherein said buffer comprises Tris.
29. The process of embodiment 25 wherein said buffer comprises Tris.
30. The process of embodiment 24 wherein said buffer comprises Tris.
31. The process of embodiment 29 wherein after said contacting step (a) said Tris buffer has a Tris concentration from about 1 mM to about 200 mM.
32. The process of embodiment 28 wherein after said contacting step (a) said Tris buffer has a Tris concentration from about 1 mM to about 200 mM.

33. The process of embodiment 31 wherein said Tris concentration is from about 10 mM to about 50 mM.
34. The process of embodiment 32 wherein said Tris concentration is from about 10 mM to about 50 mM.
35. The process of embodiment 1 wherein said growth hormone antagonist polypeptide comprises B-2036 of [SEQ. ID. NO. 1].
36. The process of embodiment 2 wherein said growth hormone antagonist polypeptide comprises B-2036 of [SEQ. ID. NO. 1].
37. The process of embodiment 25 wherein said growth hormone antagonist polypeptide comprises B-2036 of [SEQ. ID. NO. 1].
38. The process of embodiment 26 wherein said growth hormone antagonist polypeptide comprises B-2036 of [SEQ. ID. NO. 1].
39. The process of embodiment 38 wherein before said contacting step (a), said buffer has an initial combined cysteine and cystine concentration of at least about 0.1 mM.
40. The process of embodiment 37 wherein before said contacting step (a), said buffer has an initial combined cysteine and cystine concentration of at least about 0.1 mM.
41. The process of embodiment 37 wherein said combination of cysteine and cystine in said buffer and said B-2036 before said contacting step (a) have a molar ratio of moles of combined cysteine and cystine to moles of B-2036 from about 0.5 to about 1000.
42. The process of embodiment 38 wherein said combination of cysteine and cystine in said buffer and said B-2036 before said contacting step (a) have a molar ratio of moles of combined cysteine and cystine to moles of B-2036 from about 0.5 to about 1000.
43. The process of embodiment 37 wherein after said contacting step (a) said B-2036 in said buffer has a B-2036 concentration from about 0.1 mg/ml to about 30 mg/ml.
44. The process of embodiment 38 wherein after said contacting step (a) said B-2036 in said buffer has a B-2036 concentration from about 0.1 mg/ml to about 30 mg/ml.
45. The process of embodiment 43 wherein said B-2036 concentration is from about 0.5 mg/ml to about 20 mg/ml.
46. The process of embodiment 44 wherein said B-2036 concentration is from about 0.5 mg/ml to about 20 mg/ml.
47. The method of embodiment 45 wherein said B-2036 concentration is from about 1 mg/ml to about 10 mg/ml.
48. The method of embodiment 46 wherein said B-2036 concentration is from about 1 mg/ml to about 10 mg/ml.
49. The process of embodiment 37 wherein after said contacting step (a) said buffer has a pH from about 6 to about 9.
50. The process of embodiment 38 wherein after said contacting step (a) said buffer has a pH from about 6 to about 9.
51. The process of embodiment 49 wherein said pH is from about 7.5 to about 8.5.
52. The process of embodiment 50 wherein said pH is from about 7.5 to about 8.5.
53. The process of embodiment 37 wherein said buffer and said B-2036 are maintained at a temperature from about 0° C. to about 25° C. after said contacting step (a).
54. The process of embodiment 38 wherein said buffer and said B-2036 are maintained at a temperature from about 0° C. to about 25° C. after said contacting step (a).
55. The process of embodiment 53 wherein said temperature is from about 2° C. to about 8° C.
56. The process of embodiment 54 wherein said temperature is from about 2° C. to about 8° C.
57. The process of embodiment 37 wherein said contacting step (a) is conducted for a time of at least about 30 minutes.
58. The process of embodiment 38 wherein said contacting step (a) is conducted for a time of at least about 30 minutes.
59. The process of embodiment 57 wherein said time is from about 1 hour to about 24 hours.
60. The process of embodiment 58 wherein said time is from about 1 hour to about 24 hours.
61. The process of embodiment 59 wherein said time is from about 1 hour to about 4 hours.
62. The process of embodiment 60 wherein said time is from about 1 hour to about 4 hours.
63. The process of embodiment 37 wherein after said contacting step (a) said B-2036 in said buffer has a volume from about 1 L to about 5000 L.
64. The process of embodiment 38 wherein after said contacting step (a) said B-2036 in said buffer has a volume from about 1 L to about 5000 L.
65. The process of embodiment 63 wherein said volume is from about 10 L to about 500 L.
66. The process of embodiment 64 wherein said volume is from about 10 L to about 500 L.
67. The process of embodiment 65 wherein said volume is from about 100 L to about 300 L.
68. The process of embodiment 66 wherein said volume is from about 100 L to about 300 L.
69. A process for decreasing the amount of an impurity produced in recombinant production of a growth hormone antagonist polypeptide in genetically modified host cells containing cellular component(s), the process comprising the step of:
   (a) contacting a chelating agent under sufficient conditions with (1) said impurity, (2) said growth hormone antagonist polypeptide, (3) said cellular component(s) and (4) combinations thereof to decrease said amount of said impurity,
   wherein said impurity is a trisulfide isoform of said polypeptide.
70. The process of embodiment 69 further comprising the step of:
   (b) growing said host cells to produce said polypeptide, wherein said growing is conducted either before or during said contacting step (a).
71. The process of embodiment 70 further comprising the step of:
   (c) purifying said polypeptide to yield a purified polypeptide.
72. The process of embodiment 71 further comprising the step of:
   (d) pegylating said purified polypeptide.
73. The process of embodiment 70 wherein said chelating agent is selected from the group consisting of EDTA, EGTA, and DTPA.
74. The process of embodiment 69 wherein said chelating agent is selected from the group consisting of EDTA, EGTA, and DTPA.
75. The process of embodiment 73 wherein said chelating agent comprises EDTA.
76. The process of embodiment 74 wherein said chelating agent comprises EDTA.
77. The process of embodiment 75 wherein in said contacting step (a), said trisulfide isoform is contacted with said EDTA for a period of time sufficient to decrease said amount of said trisulfide isoform by at least about 10%.
78. The process of embodiment 77 wherein said period of time is sufficient to decrease said amount of said trisulfide isoform by at least about 50%.

79. The process of embodiment 76 wherein in said contacting step (a), said trisulfide isoform is contacted with said EDTA for a period of time sufficient to decrease said amount of said trisulfide isoform by at least about 10%.
80. The process of embodiment 79 wherein said period of time is sufficient to decrease said amount of said trisulfide isoform by at least about 50%.
81. The process of embodiment 69 wherein said chelating agent is provided in a buffer.
82. The process of embodiment 70 wherein said chelating agent is provided in a buffer.
83. The process of embodiment 75 wherein said EDTA is provided in a buffer.
84. The process of embodiment 76 wherein said EDTA is provided in a buffer.
85. The process of embodiment 83 wherein before said contacting step (a), said EDTA in said buffer has an initial EDTA concentration of at least about 0.01 mM.
86. The process of embodiment 84 wherein before said contacting step (a), said EDTA in said buffer has an initial EDTA concentration of at least about 0.01 mM.
87. The process of embodiment 85 wherein said initial EDTA concentration is from about 0.01 mM to about 100 mM.
88. The process of embodiment 86 wherein said initial EDTA concentration is from about 0.01 mM to about 100 mM.
89. The process of embodiment 87 wherein said initial EDTA concentration is from about 0.1 mM to about 20 mM.
90. The process of embodiment 87 wherein said initial EDTA concentration is from about 0.1 mM to about 20 mM.
91. The process of embodiment 89 wherein said initial EDTA concentration is from about 2 mM to about 10 mM.
92. The process of embodiment 89 wherein said initial EDTA concentration is from about 2 mM to about 10 mM.
93. The process of embodiment 81 wherein said buffer is selected from the group consisting of Tris, phosphate, HEPES, citric acid, triethylamine, and histidine.
94. The process of embodiment 82 wherein said buffer is selected from the group consisting of Tris, phosphate, HEPES, citric acid, triethylamine, and histidine.
95. The process of embodiment 83 wherein said buffer is selected from the group consisting of Tris, phosphate, HEPES, citric acid, triethylamine, and histidine.
96. The process of embodiment 84 wherein said buffer is selected from the group consisting of Tris, phosphate, HEPES, citric acid, triethylamine, and histidine.
97. The process of embodiment 93 wherein said buffer comprises Tris.
98. The process of embodiment 96 wherein said buffer comprises Tris.
99. The process of embodiment 95 wherein said buffer comprises Tris.
100. The process of embodiment 94 wherein said buffer comprises Tris.
101. The process of embodiment 99 wherein after said contacting step (a) said Tris buffer has a Tris concentration from about 1 mM to about 200 mM.
102. The process of embodiment 98 wherein after said contacting step (a) said Tris buffer has a Tris concentration from about 1 mM to about 200 mM.
103. The process of embodiment 101 wherein said Tris concentration is from about 10 mM to about 50 mM.
104. The process of embodiment 102 wherein said Tris concentration is from about 10 mM to about 50 mM.
105. The process of embodiment 69 wherein said growth hormone antagonist polypeptide comprises B-2036 of [SEQ. ID. NO. 1].
106. The process of embodiment 70 wherein said growth hormone antagonist polypeptide comprises B-2036 of [SEQ. ID. NO. 1].
107. The process of embodiment 95 wherein said growth hormone antagonist polypeptide comprises B-2036 of [SEQ. ID. NO. 1].
108. The process of embodiment 96 wherein said growth hormone antagonist polypeptide comprises B-2036 of [SEQ. ID. NO. 1].
109. The process of embodiment 107 wherein said EDTA is provided in a buffer and wherein before said contacting step (a), said EDTA in said buffer has an initial EDTA concentration of at least about 0.01 mM.
110. The process of embodiment 108 wherein said EDTA is provided in a buffer and wherein before said contacting step (a), said EDTA in said buffer has an initial EDTA concentration of at least about 0.01 mM.
111. The process of embodiment 107 wherein said EDTA in said buffer and said B-2036 before said contacting step (a) have a molar ratio of moles of EDTA to moles of B-2036 from about 1 to about 1,000.
112. The process of embodiment 108 wherein said EDTA in said buffer and said B-2036 before said contacting step (a) have a molar ratio of moles of EDTA to moles of B-2036 from about 1 to about 1,000.
113. The process of embodiment 111 wherein said molar ratio is from about 20 to about 1,000.
114. The process of embodiment 112 wherein said molar ratio is from about 20 to about 1,000.
115. The process of embodiment 113 wherein said molar ratio is from about 50 to about 250.
116. The process of embodiment 114 wherein said molar ratio is from about 50 to about 250.
117. The process of embodiment 107 wherein after said contacting step (a) said B-2036 in said buffer has a B-2036 concentration from about 0.1 mg/ml to about 20 mg/ml.
118. The process of embodiment 108 wherein after said contacting step (a) said B-2036 in said buffer has a B-2036 concentration from about 0.1 mg/ml to about 20 mg/ml.
119. The process of embodiment 117 wherein said B-2036 concentration is from about 0.5 mg/ml to about 5 mg/ml.
120. The process of embodiment 118 wherein said B-2036 concentration is from about 0.5 mg/ml to about 5 mg/ml.
121. The process of embodiment 107 wherein after said contacting step (a) said buffer has a pH from about 6 to about 9.
122. The process of embodiment 108 wherein after said contacting step (a) said buffer has a pH from about 6 to about 9.
123. The process of embodiment 121 wherein said pH is from about 6.5 to about 7.5.
124. The process of embodiment 122 wherein said pH is from about 6.5 to about 7.5.
125. The process of embodiment 107 wherein said buffer and said B-2036 are maintained at a temperature from about 0° C. to about 35° C. after said contacting step (a).
126. The process of embodiment 108 wherein said buffer and said B-2036 are maintained at a temperature from about 0° C. to about 35° C. after said contacting step (a).
127. The process of embodiment 125 wherein said temperature is from about 2° C. to about 15° C.
128. The process of embodiment 126 wherein said temperature is from about 2° C. to about 15° C.
129. The process of embodiment 107 wherein said contacting step (a) is conducted for a time of from about 1 hour to about 48 hours.

130. The process of embodiment 108 wherein said contacting step (a) is conducted for a time of from about 1 hour to about 48 hours.
131. The process of embodiment 129 wherein said time is from about 5 hours to about 15 hours.
132. The process of embodiment 130 wherein said time is from about 5 hours to about 15 hours.
133. The process of embodiment 107 wherein after said contacting step (a) said B-2036 in said buffer has a volume from about 1 L to about 5000 L.
134. The process of embodiment 108 wherein after said contacting step (a) said B-2036 in said buffer has a volume from about 1 L to about 5000 L.
135. The process of embodiment 133 wherein said volume is from about 200 L to about 1500 L.
136. The process of embodiment 134 wherein said volume is from about 200 L to about 1500 L.
137. A process for decreasing the amount of an impurity produced in recombinant production of a growth hormone antagonist polypeptide in genetically modified host cells containing cellular component(s), the process comprising the step of:
  (a) contacting a metal salt under sufficient conditions with (1) said impurity, (2) said growth hormone antagonist polypeptide, (3) said cellular component(s) and (4) combinations thereof to decrease said amount of said impurity,
  wherein said impurity is a trisulfide isoform of said polypeptide.
138. The process of embodiment 137 further comprising the step of:
  (b) growing said host cells to produce said polypeptide, wherein said growing is conducted either before or during said contacting step (a).
139. The process of embodiment 138 further comprising the steps of:
  (c) optionally further contacting said impurity with a mercapto compound, and
  (c') purifying said polypeptide to yield a purified polypeptide.
140. The process of embodiment 139 further comprising the step of:
  (d) pegylating said purified polypeptide.
141. The process of embodiment 138 wherein said metal salt is selected from the group consisting of an alkali metal salt, an alkaline earth metal salt, a transition metal salt, and combinations thereof.
142. The process of embodiment 137 wherein said metal salt is selected from the group consisting of an alkali metal salt, an alkaline earth metal salt, a transition metal salt, and combinations thereof.
143. The process of embodiment 141 wherein said metal salt is selected from the group consisting of potassium phosphate, potassium acetate, sodium phosphate, sodium acetate, zinc chloride, and combinations thereof.
144. The process of embodiment 142 wherein said metal salt is selected from the group consisting of potassium phosphate, potassium acetate, sodium phosphate, sodium acetate, zinc chloride, and combinations thereof.
145. The process of embodiment 143 wherein said metal salt is selected from the group consisting of sodium phosphate and ZnCl2.
146. The process of embodiment 144 wherein said metal salt is selected from the group consisting of sodium phosphate and ZnCl2.
147. The process of embodiment 137 wherein in said contacting step (a), said trisulfide isoform is contacted with said metal salt for a period of time sufficient to decrease said amount of said trisulfide isoform by at least about 10%.
148. The process of embodiment 147 wherein said period of time is sufficient to decrease said amount of said trisulfide isoform by at least about 50%.
149. The process of embodiment 138 wherein in said contacting step (a), said trisulfide isoform is contacted with said metal salt for a period of time sufficient to decrease said amount of said trisulfide isoform by at least about 10%.
150. The process of embodiment 149 wherein said period of time is sufficient to decrease said amount of said trisulfide isoform by at least about 50%.
151. The process of embodiment 137 wherein said metal salt is provided in a buffer.
152. The process of embodiment 138 wherein said metal salt is provided in a buffer.
153. The process of embodiment 151 wherein before said contacting step (a), said metal salt in said buffer has an initial metal salt concentration from about 1 mM to about 500 mM.
154. The process of embodiment 152 wherein before said contacting step (a), said metal salt in said buffer has an initial metal salt concentration from about 1 mM to about 500 mM.
155. The process of embodiment 153 wherein said initial metal salt concentration is from about 10 mM to about 150 mM.
156. The process of embodiment 154 wherein said initial metal salt concentration is from about 10 mM to about 150 mM.
157. The process of embodiment 145 wherein said metal salt comprises sodium phosphate.
158. The process of embodiment 146 wherein said metal salt comprises sodium phosphate.
159. The process of embodiment 151 wherein said buffer is selected from the group consisting of Tris, phosphate, HEPES, citric acid, triethylamine, and histidine.
160. The process of embodiment 153 wherein said buffer is selected from the group consisting of Tris, phosphate, HEPES, citric acid, triethylamine, and histidine.
161. The process of embodiment 137 wherein said growth hormone antagonist polypeptide comprises B-2036 of [SEQ. ID. NO. 1].
162. The process of embodiment 138 wherein said growth hormone antagonist polypeptide comprises B-2036 of [SEQ. ID. NO. 1].
163. The process of embodiment 160 wherein said growth hormone antagonist polypeptide comprises B-2036 of [SEQ. ID. NO. 1].
164. The process of embodiment 159 wherein said growth hormone antagonist polypeptide comprises B-2036 of [SEQ. ID. NO. 1].
165. The process of embodiment 163 wherein said metal salt comprises sodium phosphate.
166. The process of embodiment 164 wherein said metal salt comprises sodium phosphate.
167. The process of embodiment 165 wherein before said contacting step (a), said sodium phosphate has an initial sodium phosphate concentration of at least about 0.1 mM.
168. The process of embodiment 166 wherein before said contacting step (a), said sodium phosphate has an initial sodium phosphate concentration of at least about 0.1 mM.
169. The process of embodiment 163 wherein said metal salt in said buffer and said B-2036 before said contacting step (a) have a molar ratio of moles of metal salt to moles of B-2036 from about 300 to about 10,000.

170. The process of embodiment 164 wherein metal salt in said buffer and said B-2036 before said contacting step (a) have a molar ratio of moles of metal salt to moles of B-2036 from about 300 to about 10,000.
171. The process of embodiment 169 wherein said molar ratio is from about 500 to about 5,000.
172. The process of embodiment 170 wherein said molar ratio is from about 500 to about 5,000.
173. The process of embodiment 171 wherein said molar ratio is from about 500 to about 2500.
174. The process of embodiment 172 wherein said molar ratio is from about 500 to about 2500.
175. The process of embodiment 153 wherein said metal salt is sodium phosphate or potassium phosphate.
176. The process of embodiment 154 wherein said metal salt is sodium phosphate or potassium phosphate.
177. The process of embodiment 175 wherein said initial metal salt concentration is from about 10 mM to about 150 mM.
178. The process of embodiment 176 wherein said initial metal salt concentration is from about 10 mM to about 150 mM.
179. The process of embodiment 177 wherein said initial metal salt concentration is from about 25 mM to about 100 mM.
180. The process of embodiment 178 wherein said initial metal salt concentration is from about 25 mM to about 100 mM.
181. The process of embodiment 163 wherein after said contacting step (a) said B-2036 in said buffer has a B-2036 concentration from about 0.1 mg/ml to about 20 mg/ml.
182. The process of embodiment 164 wherein after said contacting step (a) said B-2036 in said buffer has a B-2036 concentration from about 0.1 mg/ml to about 20 mg/ml.
183. The process of embodiment 181 wherein said B-2036 concentration is from about 0.5 mg/ml to about 5 mg/ml.
184. The process of embodiment 182 wherein said B-2036 concentration is from about 0.5 mg/ml to about 5 mg/ml.
185. The process of embodiment 163 wherein after said contacting step (a) said buffer has a pH from about 4 to about 9.
186. The process of embodiment 184 wherein after said contacting step (a) said buffer has a pH from about 4 to about 9.
187. The process of embodiment 185 wherein said pH is from about 5.5 to about 7.5.
188. The process of embodiment 186 wherein said pH is from about 5.5 to about 7.5.
189. The process of embodiment 163 wherein said buffer and said B-2036 are maintained at a temperature from about 0° C. to about 35° C. after said contacting step (a).
190. The process of embodiment 164 wherein said buffer and said B-2036 are maintained at a temperature from about 0° C. to about 35° C. after said contacting step (a).
191. The process of embodiment 189 wherein said temperature is from about 2° C. to about 15° C.
192. The process of embodiment 190 wherein said temperature is from about 2° C. to about 15° C.
193. The process of embodiment 163 wherein said contacting step (a) is conducted for a time of from about 1 hour to about 48 hours.
194. The process of embodiment 164 wherein said contacting step (a) is conducted for a time of from about 1 hour to about 48 hours.
195. The process of embodiment 193 wherein said time is from about 5 hours to about 15 hours.
196. The process of embodiment 194 wherein said time is from about 5 hours to about 15 hours.
197. The process of embodiment 163 wherein after said contacting step (a) said B-2036 in said buffer has a volume from about 1 L to about 5000 L.
198. The process of embodiment 164 wherein after said contacting step (a) said B-2036 in said buffer has a volume from about 1 L to about 5000 L.
199. The process of embodiment 197 wherein said volume is from about 200 L to about 1500 L.
200. The process of embodiment 198 wherein said volume is from about 200 L to about 1500 L.
201. A process for decreasing the amount of an impurity produced in recombinant production of a growth hormone antagonist polypeptide in genetically modified host cells containing cellular component(s), the process comprising the step of:
  (a) contacting a chelating agent under sufficient conditions with (1) said impurity, (2) said growth hormone antagonist polypeptide, (3) said cellular component(s) and (4) combinations thereof to decrease said amount of said impurity,
  wherein said impurity is a des-phe isoform of said polypeptide.
202. The process of embodiment 201 further comprising the step of:
  (b) growing said host cells to produce said polypeptide, wherein said growing is conducted either before or during said contacting step (a).
203. The process of embodiment 202 further comprising the step of:
  (c) purifying said polypeptide to yield a purified polypeptide.
204. The process of embodiment 203 further comprising the step of:
  (d) pegylating said purified polypeptide.
205. The process of embodiment 202 wherein said chelating agent is selected from the group consisting of EDTA, EGTA, and DTPA.
206. The process of embodiment 201 wherein said chelating agent is selected from the group consisting of EDTA, EGTA, and DTPA.
207. The process of embodiment 205 wherein said chelating agent comprises EDTA.
208. The process of embodiment 206 wherein said chelating agent comprises EDTA.
209. The process of embodiment 207 wherein in said contacting step (a), said des-phe isoform is contacted with said EDTA for a period of time sufficient to decrease said amount of said des-phe isoform by at least about 10%.
210. The process of embodiment 209 wherein said period of time is sufficient to decrease said amount of said des-phe isoform by at least about 50%.
211. The process of embodiment 208 wherein in said contacting step (a), said des-phe isoform is contacted with said EDTA for a period of time sufficient to decrease said amount of said des-phe isoform by at least about 10%.
212. The process of embodiment 211 wherein said period of time is sufficient to decrease said amount of said des-phe isoform by at least about 50%.
213. The process of embodiment 201 wherein said chelating agent is provided in a buffer.
214. The process of embodiment 202 wherein said chelating agent is provided in a buffer.
215. The process of embodiment 207 wherein said EDTA is provided in a buffer.

216. The process of embodiment 208 wherein said EDTA is provided in a buffer.
217. The process of embodiment 215 wherein before said contacting step (a), said EDTA in said buffer has an initial EDTA concentration of at least about 0.01 mM.
218. The process of embodiment 216 wherein before said contacting step (a), said EDTA in said buffer has an initial EDTA concentration of at least about 0.01 mM.
219. The process of embodiment 217 wherein said initial EDTA concentration is from about 0.01 mM to about 100 mM.
220. The process of embodiment 218 wherein said initial EDTA concentration is from about 0.01 mM to about 100 mM.
221. The process of embodiment 219 wherein said initial EDTA concentration is from about 0.1 mM to about 20 mM.
222. The process of embodiment 220 wherein said initial EDTA concentration is from about 0.1 mM to about 20 mM.
223. The process of embodiment 221 wherein said initial EDTA concentration is from 2 mM to about 10 mM.
224. The process of embodiment 222 wherein said initial EDTA concentration is from 2 mM to about 10 mM.
225. The process of embodiment 213 wherein said buffer is selected from the group consisting of Tris, phosphate, HEPES, citric acid, triethylamine, and histidine.
226. The process of embodiment 214 wherein said buffer is selected from the group consisting of Tris, phosphate, HEPES, citric acid, triethylamine, and histidine.
227. The process of embodiment 215 wherein said buffer is selected from the group consisting of Tris, phosphate, HEPES, citric acid, triethylamine, and histidine.
228. The process of embodiment 216 wherein said buffer is selected from the group consisting of Tris, phosphate, HEPES, citric acid, triethylamine, and histidine.
229. The process of embodiment 225 wherein said buffer comprises Tris.
230. The process of embodiment 226 wherein said buffer comprises Tris.
231. The process of embodiment 227 wherein said buffer comprises Tris.
232. The process of embodiment 228 wherein said buffer comprises Tris.
233. The process of embodiment 229 wherein after said contacting step (a) said Tris buffer has a Tris concentration from about 1 mM to about 200 mM.
234. The process of embodiment 230 wherein after said contacting step (a) said Tris buffer has a Tris concentration from about 1 mM to about 200 mM.
235. The process of embodiment 233 wherein said Tris concentration is from about 10 mM to about 50 mM.
236. The process of embodiment 234 wherein said Tris concentration is from about 10 mM to about 50 mM.
237. The process of embodiment 201 wherein said growth hormone antagonist polypeptide comprises B-2036 of [SEQ. ID. NO. 1].
238. The process of embodiment 202 wherein said growth hormone antagonist polypeptide comprises B-2036 of [SEQ. ID. NO. 1].
239. The process of embodiment 227 wherein said growth hormone antagonist polypeptide comprises B-2036 of [SEQ. ID. NO. 1].
240. The process of embodiment 228 wherein said growth hormone antagonist polypeptide comprises B-2036 of [SEQ. ID. NO. 1].
241. The process of embodiment 239 wherein before said contacting step (a), said EDTA in said buffer has an initial EDTA concentration of at least about 0.01 mM.
242. The process of embodiment 240 wherein before said contacting step (a), said EDTA in said buffer has an initial EDTA concentration of at least about 0.01 mM.
243. The process of embodiment 239 wherein said EDTA in said buffer and said B-2036 before said contacting step (a) have a molar ratio of moles of EDTA to moles of B-2036 from about 1 to about 1,000.
244. The process of embodiment 240 wherein said EDTA in said buffer and said B-2036 before said contacting step (a) have a molar ratio of moles of EDTA to moles of B-2036 from about 1 to about 1,000.
245. The process of embodiment 243 wherein said molar ratio is from about 20 to about 1,000.
246. The process of embodiment 244 wherein said molar ratio is from about 20 to about 1,000.
247. The process of embodiment 245 wherein said molar ratio is from about 50 to about 250.
248. The process of embodiment 246 wherein said molar ratio is from about 50 to about 250.
249. The process of embodiment 239 wherein after said contacting step (a) said B-2036 in said buffer has a B-2036 concentration from about 0.1 mg/ml to about 20 mg/ml.
250. The process of embodiment 240 wherein after said contacting step (a) said B-2036 in said buffer has a B-2036 concentration from about 0.1 mg/ml to about 20 mg/ml.
251. The process of embodiment 249 wherein said B-2036 concentration is from about 0.5 mg/ml to about 5 mg/ml.
252. The process of embodiment 250 wherein said B-2036 concentration is from about 0.5 mg/ml to about 5 mg/ml.
253. The process of embodiment 249 wherein said B-2036 concentration is from about 1 mg/ml to about 10 mg/ml.
254. The process of embodiment 250 wherein said B-2036 concentration is from about 1 mg/ml to about 10 mg/ml.
255. The process of embodiment 239 wherein after said contacting step (a) said buffer has a pH from about 6 to about 9.
256. The process of embodiment 240 wherein after said contacting step (a) said buffer has a pH from about 6 to about 9.
257. The process of embodiment 255 wherein said pH is from about 6.5 to about 7.5.
258. The process of embodiment 256 wherein said pH is from about 6.5 to about 7.5.
259. The process of embodiment 239 wherein said buffer and said B-2036 are maintained at a temperature from about 0° C. to about 35° C. after said contacting step (a).
260. The process of embodiment 240 wherein said buffer and said B-2036 are maintained at a temperature from about 0° C. to about 35° C. after said contacting step (a).
261. The process of embodiment 259 wherein said temperature is from about 2° C. to about 15° C.
262. The process of embodiment 260 wherein said temperature is from about 2° C. to about 15° C.
263. The process of embodiment 239 wherein said contacting step (a) is conducted for a time of from about 1 hour to about 48 hours.
264. The process of embodiment 240 wherein said contacting step (a) is conducted for a time of from about 1 hour to about 48 hours.
265. The process of embodiment 263 wherein said time is from about 5 hours to about 15 hours.
266. The process of embodiment 264 wherein said time is from about 5 hours to about 15 hours.

267. The process of embodiment 239 wherein after said contacting step (a) said B-2036 in said buffer has a volume from about 1 L to about 5000 L.
268. The process of embodiment 240 wherein after said contacting step (a) said B-2036 in said buffer has a volume from about 1 L to about 5000 L.
269. The process of embodiment 267 wherein said volume is from about 200 L to about 1500 L.
270. The process of embodiment 268 wherein said volume is from about 200 L to about 1500 L.
271. A process for decreasing the amount of an impurity produced in recombinant production of a growth hormone antagonist polypeptide in genetically modified host cells containing cellular component(s), the process comprising the step of:
    (a) contacting a metal salt under sufficient conditions with (1) said impurity, (2) said growth hormone antagonist polypeptide, (3) said cellular component(s) and (4) combinations thereof to decrease said amount of said impurity,
    wherein said impurity is a des-phe isoform of said polypeptide.
272. The process of embodiment 271 further comprising the step of:
    (b) growing said host cells to produce said polypeptide, wherein said growing is conducted either before or during said contacting step (a).
273. The process of embodiment 272 further comprising the steps of:
    (c) optionally further contacting said impurity with a mercapto compound, and
    (c') purifying said polypeptide to yield a purified polypeptide.
274. The process of embodiment 273 further comprising the step of:
    (d) pegylating said purified polypeptide.
275. The process of embodiment 272 wherein said metal salt is selected from the group consisting of an alkali metal salt, an alkaline earth metal salt, a transition metal salt, and combinations thereof.
276. The process of embodiment 271 wherein said metal salt is selected from the group consisting of an alkali metal salt, an alkaline earth metal salt, a transition metal salt, and combinations thereof.
277. The process of embodiment 275 wherein said metal salt is selected from the group consisting of potassium phosphate, potassium acetate, sodium phosphate, sodium acetate, zinc chloride, and combinations thereof.
278. The process of embodiment 276 wherein said metal salt is selected from the group consisting of potassium phosphate, potassium acetate, sodium phosphate, sodium acetate, zinc chloride, and combinations thereof.
279. The process of embodiment 277 wherein said metal salt is selected from the group consisting of sodium phosphate and ZnCl2.
280. The process of embodiment 278 wherein said metal salt is selected from the group consisting of sodium phosphate and ZnCl2.
281. The process of embodiment 271 wherein in said contacting step (a), said des-phe isoform is contacted with said metal salt for a period of time sufficient to decrease said amount of said des-phe isoform by at least about 10%.
282. The process of embodiment 281 wherein said period of time is sufficient to decrease said amount of said des-phe isoform by at least about 50%.
283. The process of embodiment 272 wherein in said contacting step (a), said des-phe isoform is contacted with said metal salt for a period of time sufficient to decrease said amount of said des-phe isoform by at least about 10%.
284. The process of embodiment 283 wherein said period of time is sufficient to decrease said amount of said des-phe isoform by at least 50%.
285. The process of embodiment 271 wherein said metal salt is provided in a buffer.
286. The process of embodiment 272 wherein said metal salt is provided in a buffer.
287. The process of embodiment 285 wherein before said contacting step (a), said metal salt in said buffer has an initial metal salt concentration from about 1 mM to about 500 mM.
288. The process of embodiment 286 wherein before said contacting step (a), said metal salt in said buffer has an initial metal salt concentration from about 1 mM to about 500 mM.
289. The process of embodiment 287 wherein said initial metal salt concentration is from about 10 mM to about 150 mM.
290. The process of embodiment 288 wherein said initial metal salt concentration is from about 10 mM to about 150 mM.
291. The process of embodiment 286 wherein said metal salt comprises sodium phosphate.
292. The process of embodiment 285 wherein said metal salt comprises sodium phosphate.
293. The process of embodiment 285 wherein said buffer is selected from the group consisting of Tris, phosphate, HEPES, citric acid, triethylamine, and histidine.
294. The process of embodiment 286 wherein said buffer is selected from the group consisting of Tris, phosphate, HEPES, citric acid, triethylamine, and histidine.
295. The process of embodiment 271 wherein said growth hormone antagonist polypeptide comprises B-2036 of [SEQ. ID. NO. 1].
296. The process of embodiment 272 wherein said growth hormone antagonist polypeptide comprises B-2036 of [SEQ. ID. NO. 1].
297. The process of embodiment 295 wherein said metal salt comprises sodium phosphate.
298. The process of embodiment 296 wherein said metal salt comprises sodium phosphate.
299. The process of embodiment 297 wherein before said contacting step (a), said sodium phosphate has an initial sodium phosphate concentration of at least about 0.1 mM.
300. The process of embodiment 298 wherein before said contacting step (a), said sodium phosphate has an initial sodium phosphate concentration of at least about 0.1 mM.
301. The process of embodiment 295 wherein said metal salt and said B-2036 before said contacting step (a) have a molar ratio of moles of metal salt to moles of B-2036 from about 300 to about 10,000.
302. The process of embodiment 296 wherein said metal salt and said B-2036 before said contacting step (a) have a molar ratio of moles of metal salt to moles of B-2036 from about 300 to about 10,000.
303. The process of embodiment 301 wherein said molar ratio is from about 500 to about 5000.
304. The process of embodiment 302 wherein said molar ratio is from about 500 to about 5,000.
305. The process of embodiment 303 wherein said molar ratio is from about 500 to about 2500.
306. The process of embodiment 304 wherein said molar ratio is from about 500 to about 2500.
307. The process of embodiment 287 wherein said metal salt is sodium phosphate or potassium phosphate.

308. The process of embodiment 288 wherein said metal salt is sodium phosphate or potassium phosphate.

309. The process of embodiment 307 wherein said initial metal salt concentration is from about 10 mM to about 150 mM.

310. The process of embodiment 308 wherein said initial metal salt concentration is from about 10 mM to about 150 mM.

311. The process of embodiment 309 wherein said initial metal salt concentration is from about 25 mM to about 100 mM sodium phosphate.

312. The process of embodiment 310 wherein said initial metal salt concentration is from about 25 mM to about 100 mM.

313. The process of embodiment 295 wherein after said contacting step (a) said B-2036 has a B-2036 concentration from about 0.1 mg/ml to about 20 mg/ml.

314. The process of embodiment 296 wherein after said contacting step (a) said B-2036 has a B-2036 concentration from about 0.1 mg/ml to about 20 mg/ml.

315. The process of embodiment 313 wherein said B-2036 concentration is from about 0.5 mg/ml to about 5 mg/ml.

316. The process of embodiment 314 wherein said B-2036 concentration is from about 0.5 mg/ml to about 5 mg/ml.

317. The process of embodiment 293 wherein after said contacting step (a) said buffer has a pH from about 4 to about 9.

318. The process of embodiment 294 wherein after said contacting step (a) said buffer has a pH from about 4 to about 9.

319. The process of embodiment 317 wherein said pH is from about 5.5 to about 7.5.

320. The process of embodiment 318 wherein said pH is from about 5.5 to about 7.5.

321. The process of embodiment 295 wherein said buffer and said B-2036 are maintained at a temperature from about 0° C. to about 35° C. after said contacting step (a).

322. The process of embodiment 296 wherein said buffer and said B-2036 are maintained at a temperature from about 0° C. to about 35° C. after said contacting step (a).

323. The process of embodiment 321 wherein said temperature is from about 2° C. to about 15° C.

324. The process of embodiment 322 wherein said temperature is from about 2° C. to about 15° C.

325. The process of embodiment 295 wherein said contacting step (a) is conducted for a time of from about 1 hour to about 48 hours.

326. The process of embodiment 296 wherein said contacting step (a) is conducted for a time of from about 1 hour to about 48 hours.

327. The process of embodiment 325 wherein said time is from about 5 hours to about 15 hours.

328. The process of embodiment 326 wherein said time is from about 5 hours to about 15 hours.

329. The process of embodiment 295 wherein after said contacting step (a) said B-2036 in said buffer has a volume from about 1 L to about 5000 L.

330. The process of embodiment 296 wherein after said contacting step (a) said B-2036 in said buffer has a volume from about 1 L to about 5000 L.

331. The process of embodiment 329 wherein said volume is from about 200 L to about 1500

332. The process of embodiment 330 wherein said volume is from about 200 L to about 1500 L.

333. A process for decreasing the amount of an impurity produced in recombinant production of a growth hormone polypeptide in genetically modified host cells containing cellular component(s), the process comprising the step of:
(a) contacting a chelating agent under sufficient conditions with (1) said impurity, (2) said growth hormone polypeptide, (3) said cellular component(s) and (4) combinations thereof to decrease said amount of said impurity,
wherein said impurity is a des-phe isoform of said polypeptide.

334. The process of embodiment 333 further comprising the step of:
(b) growing said host cells to produce said polypeptide, wherein said growing is conducted either before or during said contacting step (a).

335. The process of embodiment 334 further comprising the step of:
(c) purifying said polypeptide to yield a purified polypeptide.

336. The process of embodiment 333 wherein said chelating agent is selected from the group consisting of EDTA, EGTA, and DTPA.

337. The process of embodiment 334 wherein said chelating agent is selected from the group consisting of EDTA, EGTA, and DTPA.

338. The process of embodiment 336 wherein said chelating agent comprises EDTA.

339. The process of embodiment 337 wherein said chelating agent comprises EDTA.

340. The process of embodiment 338 wherein in said contacting step (a), said des-phe isoform is contacted with said EDTA for a period of time sufficient to decrease said amount of said des-phe isoform by at least about 10%.

341. The process of embodiment 340 wherein said period of time is sufficient to decrease said amount of said des-phe isoform by at least about 50%.

342. The process of embodiment 339 wherein in said contacting step (a), said des-phe isoform is contacted with said EDTA for a period of time sufficient to decrease said amount of said des-phe isoform by at least about 10%.

343. The process of embodiment 342 wherein said period of time is sufficient to decrease said amount of said des-phe isoform by at least about 50%.

344. The process of embodiment 333 wherein said chelating agent is provided in a buffer.

345. The process of embodiment 334 wherein said chelating agent is provided in a buffer.

346. The process of embodiment 338 wherein said EDTA is provided in a buffer.

347. The process of embodiment 339 wherein said EDTA is provided in a buffer.

348. The process of embodiment 346 wherein before said contacting step (a), said EDTA in said buffer has an initial EDTA concentration of at least about 0.01 mM.

349. The process of embodiment 347 wherein before said contacting step (a), said EDTA in said buffer has an initial EDTA concentration of at least about 0.01 mM.

350. The process of embodiment 348 wherein said initial EDTA concentration is from about 0.01 mM to about 100 mM.

351. The process of embodiment 349 wherein said initial EDTA concentration is from about 0.01 mM to about 100 mM.

352. The process of embodiment 350 wherein said initial EDTA concentration is from about 0.1 mM to about 20 mM.

353. The process of embodiment 351 wherein said initial EDTA concentration is from about 0.1 mM to about 20 mM.
354. The process of embodiment 352 wherein said initial EDTA concentration is from 2 mM to about 10 mM.
355. The process of embodiment 353 wherein said initial EDTA concentration is from 2 mM to about 10 mM.
356. The process of embodiment 344 wherein said buffer is selected from the group consisting of Tris, phosphate, HEPES, citric acid, triethylamine, and histidine.
357. The process of embodiment 345 wherein said buffer is selected from the group consisting of Tris, phosphate, HEPES, citric acid, triethylamine, and histidine.
358. The process of embodiment 346 wherein said buffer is selected from the group consisting of Tris, phosphate, HEPES, citric acid, triethylamine, and histidine.
359. The process of embodiment 347 wherein said buffer is selected from the group consisting of Tris, phosphate, HEPES, citric acid, triethylamine, and histidine.
360. The process of embodiment 356 wherein said buffer comprises Tris.
361. The process of embodiment 357 wherein said buffer comprises Tris.
362. The process of embodiment 358 wherein said buffer comprises Tris.
363. The process of embodiment 359 wherein said buffer comprises Tris.
364. The process of embodiment 360 wherein after said contacting step (a) said Tris buffer has a Tris concentration from about 1 mM to about 200 mM.
365. The process of embodiment 361 wherein after said contacting step (a) said Tris buffer has a Tris concentration from about 1 mM to about 200 mM.
366. The process of embodiment 364 wherein said Tris concentration is from about 10 mM to about 50 mM.
367. The process of embodiment 365 wherein said Tris concentration is from about 10 mM to about 50 mM.
368. The process of embodiment 333 wherein said growth hormone comprises a polypeptide hGH of [SEQ. ID. NO. 2].
369. The process of embodiment 334 wherein said growth hormone comprises a polypeptide hGH of [SEQ. ID. NO. 2].
370. The process of embodiment 368 wherein said chelating agent comprises EDTA.
371. The process of embodiment 369 wherein said chelating agent comprises EDTA.
372. The process of embodiment 370 wherein said EDTA is provided in a buffer and wherein before said contacting step (a), said EDTA in said buffer has an initial EDTA concentration of at least about 0.01 mM.
373. The process of embodiment 371 wherein said EDTA is provided in a buffer and wherein before said contacting step (a), said EDTA in said buffer has an initial EDTA concentration of at least about 0.1 mM.
374. The process of embodiment 370 wherein said EDTA and said hGH before said contacting step (a) have a molar ratio of moles of EDTA to moles of hGH from about 1 to about 1,000.
375. The process of embodiment 371 wherein said EDTA and said hGH before said contacting step (a) have a molar ratio of moles of EDTA to moles of hGH from about 1 to about 1,000.
376. The process of embodiment 374 wherein said molar ratio is from about 20 to about 1,000.
377. The process of embodiment 375 wherein said molar ratio is from about 20 to about 1,000.
378. The process of embodiment 376 wherein said molar ratio is from about 50 to about 250.
379. The process of embodiment 377 wherein said molar ratio is from about 50 to about 250.
380. The process of embodiment 368 wherein after said contacting step (a) said hGH has an hGH concentration from about 0.1 mg/ml to about 20 mg/ml.
381. The process of embodiment 369 wherein after said contacting step (a) said hGH has an hGH concentration from about 0.1 mg/ml to about 20 mg/ml.
382. The process of embodiment 380 wherein said hGH concentration is from about 0.5 mg/ml to about 5 mg/ml.
383. The process of embodiment 381 wherein said hGH concentration is from about 0.5 mg/ml to about 5 mg/ml.
384. The process of embodiment 368 wherein said chelating agent is provided in a buffer and wherein after said contacting step (a) said buffer has a pH from about 6 to about 9.
385. The process of embodiment 369 wherein said chelating agent is provided in a buffer and wherein after said contacting step (a) said buffer has a pH from about 6 to about 9.
386. The process of embodiment 384 wherein said pH is from about 6.5 to about 7.5.
387. The process of embodiment 385 wherein said pH is from about 6.5 to about 7.5.
388. The process of embodiment 368 wherein said chelating agent is provided in a buffer and wherein said buffer and said hGH is maintained at a temperature from about 0° C. to about 35° C. after said contacting step (a).
389. The process of embodiment 369 wherein said chelating agent is provided in a buffer and wherein said buffer and said hGH is maintained at a temperature from about 0° C. to about 35° C. after said contacting step (a).
390. The process of embodiment 388 wherein said temperature is from about 2° C. to about 15° C.
391. The process of embodiment 389 wherein said temperature is from about 2° C. to about 15° C.
392. The process of embodiment 368 wherein said contacting step (a) is conducted for a time of from about 1 hour to about 48 hours.
393. The process of embodiment 369 wherein said contacting step (a) is conducted for a time of from about 1 hour to about 48 hours.
394. The process of embodiment 392 wherein said time is from about 5 hours to about 15 hours.
395. The process of embodiment 393 wherein said time is from about 5 hours to about 15 hours.
396. The process of embodiment 368 wherein said chelating agent is provided in a buffer and wherein after said contacting step (a) said hGH in said buffer has a volume from about 1 L to about 5000 L.
397. The process of embodiment 369 wherein said chelating agent is provided in a buffer and wherein after said contacting step (a) said hGH in said buffer has a volume from about 1 L to about 5000 L.
398. The process of embodiment 396 wherein said volume is from about 200 L to about 1500 L.
399. The process of embodiment 397 wherein said volume is from about 200 L to about 1500 L.
400. A process for decreasing the amount of an impurity produced in recombinant production of a growth hormone polypeptide in genetically modified host cells containing cellular component(s), the process comprising the step of:
 (a) contacting a metal salt under sufficient conditions with
  (1) said impurity, (2) said growth hormone polypeptide, (3) said cellular component(s) and (4) combinations thereof u to decrease said amount of said impurity, wherein said impurity is a des-phe isoform of said polypeptide.

401. The process of embodiment 430 further comprising the step of:
(b) growing said host cells to produce said polypeptide, wherein said growing is conducted either before or during said contacting step (a).

402. The process of embodiment 401 further comprising the steps of:
(c) optionally further contacting said impurity with a mercapto compound, and
(c') purifying said polypeptide to yield a purified polypeptide.

403. The process of embodiment 400 wherein said metal salt is selected from the group consisting of an alkali metal salt, an alkaline earth metal salt, a transition metal salt, and combinations thereof.

404. The process of embodiment 401 wherein said metal salt is selected from the group consisting of an alkali metal salt, an alkaline earth metal salt, a transition metal salt, and combinations thereof.

405. The process of embodiment 403 wherein said metal salt is selected from the group consisting of potassium phosphate, potassium acetate, sodium phosphate, sodium acetate, zinc chloride, and combinations thereof.

406. The process of embodiment 404 wherein said metal salt is selected from the group consisting of potassium phosphate, potassium acetate, sodium phosphate, sodium acetate, zinc chloride, and combinations thereof.

407. The process of embodiment 405 wherein said metal salt is selected from the group consisting of sodium phosphate and $ZnCl_2$.

408. The process of embodiment 406 wherein said metal salt is selected from the group consisting of sodium phosphate and ZnCl2.

409. The process of embodiment 400 wherein in said contacting step (a), said des-phe isoform is contacted with said metal salt for a period of time sufficient to decrease said amount of said des-phe isoform by at least about 10%.

410. The process of embodiment 409 wherein said period of time is sufficient to decrease said amount of des-phe isoform by at least about 50%.

411. The process of embodiment 401 wherein in said contacting step (a), said des-phe isoform is contacted with said metal salt for a period of time sufficient to decrease said amount of said des-phe isoform by at least about 10%.

412. The process of embodiment 411 wherein said period of time is sufficient to decrease said amount of des-phe isoform by at least about 50%.

413. The process of embodiment 400 wherein said metal salt is provided in a buffer.

414. The process of embodiment 401 wherein said metal salt is provided in a buffer.

415. The process of embodiment 413 wherein before said contacting step (a), said metal salt in said buffer has an initial metal salt concentration from about 1 mM to about 500 mM.

416. The process of embodiment 414 wherein before said contacting step (a), said metal salt in said buffer has an initial metal salt concentration from about 1 mM to about 500 mM.

417. The process of embodiment 415 wherein said initial metal salt concentration is from about 10 mM to about 150 mM.

418. The process of embodiment 416 wherein said initial metal salt concentration is from about 10 mM to about 150 mM.

419. The process of embodiment 417 wherein said metal salt comprises sodium phosphate.

420. The process of embodiment 418 wherein said metal salt comprises sodium phosphate.

421. The process of embodiment 413 wherein said buffer is selected from the group consisting of Tris, phosphate, HEPES, citric acid, triethylamine, and histidine.

422. The process of embodiment 414 wherein said buffer is selected from the group consisting of Tris, phosphate, HEPES, citric acid, triethylamine, and histidine.

423. The process of embodiment 400 wherein said growth hormone comprises a polypeptide hGH of [SEQ. ID. NO. 2].

424. The process of embodiment 401 wherein said growth hormone comprises a polypeptide hGH of [SEQ. ID. NO. 2].

425. The process of embodiment 407 wherein said metal salt comprises sodium phosphate.

426. The process of embodiment 408 wherein said metal salt comprises sodium phosphate.

427. The process of embodiment 425 wherein before said contacting step (a), said sodium phosphate has an initial sodium phosphate concentration of at least about 0.1 mM.

428. The process of embodiment 426 wherein before said contacting step (a), said sodium phosphate has an initial sodium phosphate concentration of at least about 0.1 mM.

429. The process of embodiment 423 wherein said metal salt in said buffer and said hGH before said contacting step (a) have a molar ratio of moles of metal salt to moles of hGH from about 300 to about 10,000.

430. The process of embodiment 424 wherein said metal salt in said buffer and said hGH before said contacting step (a) have a molar ratio of moles of metal salt to moles of hGH from about 300 to about 10,000.

431. The process of embodiment 429 wherein said molar ratio is from about 500 to about 5,000.

432. The process of embodiment 430 wherein said molar ratio is from about 500 to about 5,000.

433. The process of embodiment 431 wherein said molar ratio is from about 500 to about 2500.

434. The process of embodiment 432 wherein said molar ratio is from about 500 to about 2500.

435. The process of embodiment 415 wherein said metal salt is sodium phosphate or potassium phosphate.

436. The process of embodiment 416 wherein said metal salt is sodium phosphate or potassium phosphate.

437. The process of embodiment 435 wherein said initial metal salt concentration is from about 10 mM to about 150 mM.

438. The process of embodiment 436 wherein said initial metal salt concentration is from about 10 mM to about 150 mM.

439. The process of embodiment 437 wherein said initial metal salt concentration is from about 25 mM to about 100 mM.

440. The process of embodiment 438 wherein said initial metal salt concentration is from about 25 mM to about 100 mM.

441. The process of embodiment 423 wherein after said contacting step (a) said hGH in said buffer has an hGH concentration from about 0.1 mg/ml to about 20 mg/ml.

442. The process of embodiment 424 wherein after said contacting step (a) said hGH in said buffer has an hGH concentration from about 0.1 mg/ml to about 20 mg/ml.

443. The process of embodiment 441 wherein said hGH concentration is from about 0.5 mg/ml to about 5 mg/ml.
444. The process of embodiment 442 wherein said hGH concentration is from about 0.5 mg/ml to about 5 mg/ml.
445. The process of embodiment 413 wherein after said contacting step (a) said buffer has a pH from about 4 to about 9.
446. The process of embodiment 414 wherein after said contacting step (a) said buffer has a pH from about 4 to about 9.
447. The process of embodiment 445 wherein said pH is from about 5.5 to about 7.5.
448. The process of embodiment 446 wherein said pH is from about 5.5 to about 7.5.
449. The process of embodiment 423 wherein said metal salt is provided in a buffer and wherein said buffer and said hGH is maintained at a temperature from about 0° C. to about 35° C. after said contacting step (a).
450. The process of embodiment 424 wherein said metal salt is provided in a buffer and wherein said buffer and said hGH is maintained at a temperature from about 0° C. to about 35° C. after said contacting step (a).
451. The process of embodiment 449 wherein said temperature is from about 2° C. to about 15° C.
452. The process of embodiment 450 wherein said temperature is from about 2° C. to about 15° C.
453. The process of embodiment 423 wherein said contacting step (a) is conducted for a time of from about 1 hour to about 48 hours.
454. The process of embodiment 424 wherein said contacting step (a) is conducted for a time of from about 1 hour to about 48 hours.
455. The process of embodiment 453 wherein said time is from about 5 hours to about 15 hours.
456. The process of embodiment 454 wherein said time is from about 5 hours to about 15 hours.
457. The process of embodiment 423 wherein after said contacting step (a) said hGH in said buffer has a volume from about 1 L to about 5000 L.
458. The process of embodiment 424 wherein after said contacting step (a) said hGH in said buffer has a volume from about 1 L to about 5000 L.
459. The process of embodiment 457 wherein said volume is from about 200 L to about 1500 L.
460. The process of embodiment 458 wherein said volume is from about 200 L to about 1500
461. The process of embodiment 69, wherein said contacting step (a) is conducted in the absence of a mercapto compound.
462. The process of embodiment 69, wherein said contacting step (a) further comprises contacting with said chelating agent followed by contacting with a mercapto compound in the absence of said chelating agent.
463. The process of embodiment 462, wherein said mercapto compound is selected from the group consisting of sulfites, glutathione, beta-mercaptoethanol, dithiothreitol, mercaptoethylamine, dithioerythritol, tris(2-carboxyethyl) phosphine hydrochloride, cysteine, and cysteine in combination with cystine.
464. The process of embodiment 463, wherein said mercapto compound comprises cysteine or cysteine in combination with cystine.
465. The process of embodiment 137, wherein said contacting step (a) further comprises contacting with said metal salt in combination with a mercapto compound.
466. The process of embodiment 465, wherein said mercapto compound is selected from the group consisting of sulfites, glutathione, beta-mercaptoethanol, dithiothreitol, mercaptoethylamine, dithioerythritol, tris(2-carboxyethyl) phosphine hydrochloride, cysteine, and cysteine in combination with cystine.
467. The process of embodiment 466, wherein said mercapto compound comprises cysteine or cysteine in combination with cystine.
468. The process of embodiment 137, wherein said contacting step (a) further comprises contacting with said metal salt followed by contacting with a mercapto compound in the absence or presence of said metal salt.

The following is presented by way of example and is not to be construed as a limitation to the scope of the invention. All citations to books, magazines, journal articles, patents, or any other publications, etc., recited in this application are expressly incorporated herein by reference.

EXAMPLES

Example 1

Decrease of Trisulfide Isoform Impurity of Growth Hormone Antagonist (GHA) with Mercapto Compound(s)

Reduction of B-2036-trisulfide level was accomplished using Retentate 1 (see FIG. 2 flowchart 1 below) in the B-2036 purification process. Fermentation of the recombinant *E. coli* expressing B-2036 was carried out as described by Cunningham et al. in U.S. Pat. No. 5,849,535. The initial extraction and purification steps (all steps conducted prior to obtaining Retentate 1 in FIG. 2 flowchart 1 below, e.g., all resuspension and homogenization, two-phase extraction, reversed phase chromatography, and anion exchange chromatography) were carried out as described in the accompanying flowchart 1 (FIG. 2). Following the first ultrafiltration/diafiltration step, the product was present in 25 mM HEPES, pH 7.0 buffer (~150 L) at a protein concentration of 3.7 g/L. The temperature of the product solution was cooled to 2 to 8° C. and it was treated with a $\frac{1}{10}^{th}$ volume addition (~15 L) of freshly prepared 200 mM Tris, 20 mM cysteine, pH 8.0 buffer that had been cooled to 2 to 8° C. The B-2036/cysteine solution was maintained at 2 to 8° C. and mixed for 174 minutes. The mixture was then concentrated to 131 L using Millipore Biomax 5 ultrafiltration membranes and diafiltered against a 6× volume of 25 mM HEPES, pH 7.0. The resulting product was then carried through the remainder of the B-2036 purification process as described in FIG. 2 flowchart 1 below.

Before the cysteine incubation, the B-2036/trisulfide level was measured to be 3.7 area percent. Immediately after the cysteine incubation, its level dropped to 2.0 area percent (decreased by about 46%).

Example 2

Decrease of Trisulfide Isoform Impurity of Growth Hormone Antagonist with Chelating Agent(s)

Referring to FIG. 2 flowchart 1, 165 Kg of frozen GHA cell paste cell paste were added to ~1013 liters of 150 mM Tris, 5 mM EDTA, pH 7.2. When the cell paste had finished thawing (determined by stable $A_{550}$ readings) the mixture was passed through a Niro homogenizer at 950+/−50 Bar at a nominal flowrate of 250 l/hour. The homogenate was collected in a tank where the temperature was maintained between 24 and 33° C. Ammonium sulfate and PEG-4600 were added to the lysate mixture to form a concentration of 10% (w/w) of both compounds. The resulting two-phase mixture was mixed for 60-120 minutes and then these phases were resolved by passing the solution through a liquid/liquid, solids discharging centrifuge. The top phase contained the desired product and was collected and filtered through a filter train consisting of a "delipidating" filter, "depth" filter, and a 0.2 µm filter. The filtrate was collected in three separate totes and samples of each were analyzed for B-2036-trisulfide. The levels ranged from 3.1 to 3.8 area percent. The resulting material was then processed to bulk intermediate using the procedure outlined in the flowchart of Example #1 (FIG. 2).

By comparison, samples from lots processed by the above-noted procedure (but without the EDTA component (chelating agent) in the lysis buffer and without cysteine treatment of Retentate 1) yielded a trisulfide level (n=10) ranging from 3.2 to 6.4 area percent with a mean of 5.1 at the end of the entire process of FIG. 2 flowchart 1. When EDTA was included in the lysis buffer, and the cysteine incubation step of retentate 1 was conducted, the trisulfide level at the end of the entire process of FIG. 2 flowchart 1 was 1.5% area percent.

Example 3

Decrease of Trisulfide Isoform Impurity of Growth Hormone Antagonist with Metal Salt(s)

Referring to FIG. 3 flowchart 2 below, 165 Kg of frozen cell paste cell paste were added to ~1013 liters of 100 mM sodium phosphate, pH 6.0. When the cell paste had finished thawing (determined by stable $A_{550}$ readings) the mixture was passed through a Niro homogenizer at 950+/−50 bar at a nominal flowrate of 250 l/hour. The homogenate was collected in a tank where the temperature was maintained between 24 and 33° C. Ammonium sulfate and PEG-4600 were added to the lysate mixture to form a concentration of 10% (w/w) of both compounds. The resulting two-phase mixture was mixed for 60-120 minutes and then these phases were resolved by passing the solution through a liquid/liquid, solids discharging centrifuge. The top phase contained the desired product and was collected and filtered through a filter train consisting of a "delipidating" filter, a "depth" filter, and a 0.2 µm filter. The material was carried through the remainder of the B-2036 process as described in FIG. 3 flowchart 2 below. The level of B-2036-trisulfide present at the end of processing was 1.4 area percent. This compared with B-2036-trisulfide levels of 3.2 to 6.4 area percent (mean=5.1 area percent) for B-2036 lots (n=10) processed with the normal lysis buffer (150 mM Tris, pH 7.2).

Example 4

Decrease of Des-Phe Isoform Impurity of Growth Hormone Antagonist with Chelating Agent(s)

Referring to FIG. 2 flowchart 1, 165 Kg of frozen cell paste cell paste were added to ~1013 liters of 150 mM Tris, 5 mM EDTA, pH 7.2. When the cell paste had finished thawing (determined by stable $A_{550}$ readings) the mixture was passed through a Niro homogenizer at 950+/−50 Bar at a nominal flowrate of 250 l/hour. The homogenate was collected in a tank where the temperature was maintained between 24 and 33° C. Ammonium sulfate and PEG-4600 were added to the lysate mixture to form a concentration of 10% (w/w) of both compounds. The resulting two-phase mixture was mixed for 60-120 minutes and then these phases were resolved by passing the solution through a liquid/liquid, solids discharging centrifuge. The top phase contained the desired product and was collected and filtered through a filter train consisting of a "delipidating" filter, a "depth" filter, and a 0.2 µm filter. The filtrate (obtained after top phase filtration; see FIG. 2 flowchart 1) was collected in three separate totes and samples of each were analyzed for B-2036/des-phe. The levels ranged from 3.2 to 6.3 area percent. For comparison, further processing according to FIG. 2 flowchart 1 further reduced the B-2036 des-phe level to 0.3 area percent of Retentate 3. This further reduction of B-2036 des-phe level was achieved by the product collection parameters of the second anion exchange chromatography step. When the lysis buffer included EDTA and the collection procedures of the ion exchange chromatography step were conducted, B-2036/des-phe levels of 0.3 are a percent were obtained as compared to the final process levels of 4.6 to 16.2 area percent (mean=10.2 area percent) for B-2036 lots (n=10) processed without EDTA (e.g., 150 mM Tris, pH 7.2) and without the above-noted collection procedures.

Example 5

Decrease of Des-Phe Isoform Impurity of Growth Hormone Antagonist with Metal Salt(s)

Referring to FIG. 3 flowchart 2, 165 Kg of frozen cell paste cell paste were added to ~1013 liters of 100 mM sodium phosphate, pH 6.0. When the cell paste had finished thawing (determined by stable $A_{550}$ readings) the mixture was passed through a Niro homogenizer at 950+/−50 bar at a nominal flowrate of 250 l/hour. The homogenate was collected in a tank where the temperature was maintained between 24 and 33° C. Ammonium sulfate and PEG-4600 were added to the lysate mixture to form a concentration of 10% (w/w) of both compounds. The resulting two-phase mixture was mixed for 60-120 minutes and then these phases were resolved by passing the solution through a liquid/liquid, solids discharging centrifuge. The top phase contained the desired product and was collected and filtered through a filter train consisting of a "delipidating" filter, a "depth" filter, and a 0.2 µm filter. The filtrate was collected in three separate totes and samples of each were analyzed for B-2036/des-phe. The levels ranged from 6.0 to 9.4 area percent. For comparison, further processing according to FIG. 3 flowchart 2 further reduced the B-2036/des-phe level to 0.8 area percent of Retentate 2. This further reduction of B-2036/des-phe level was achieved by the product collection parameters following the second anion exchange chromatography step. When the lysis buffer included sodium phosphate and the collection procedures of the second ion-exchange chromatography step were conducted, the B-2036/des-phe level of 0.8 area percent was obtained as compared to the final process levels of 4.6 to 16.2 area percent (mean=10.2 area percent) for B-2036 lots (n=10) processed without sodium phosphate (e.g., 150 mM Tris, pH 7.2) and without the above-noted collection procedures.

Example 6

Decrease of Des-Phe Isoform Impurity of Growth Hormone Agonist with Chelating Agent(s)

Suspend fresh or frozen recombinant cells expressing growth hormone agonist in a buffer containing EDTA. Then disrupt the cells either completely by a process such as homogenization, or partially in a process such as osmotic shock or freeze/thaw to release the growth hormone agonist. Then isolate the disrupted solution by two-phase extraction, solid/liquid centrifugation, or filtration. Purify the agonist by a series of liquid chromatography steps.

Example 7

Decrease of Des-Phe Isoform Impurity of Growth Hormone Agonist with Metal Salt(s)

Suspend fresh or frozen recombinant cells expressing growth hormone agonist in a buffer containing sodium phosphate. Then disrupt the cells either completely by a process such as homogenization, or partially in a process such as osmotic shock or freeze/thaw to release the growth hormone agonist. Then isolate the disrupted solution by two-phase extraction, solid/liquid centrifugation, or filtration. Purify the agonist by a series of liquid chromatography steps.

---

What is claimed is:

1. A process for decreasing the amount of an impurity produced in recombinant production of a growth hormone antagonist polypeptide B-2036 of SEQ ID NO:1 in genetically modified host cells containing cellular component(s), the process comprising the step of:
   (a) contacting a chelating agent with a cell lysate or cell paste lysate comprising (1) said impurity, (2) said growth hormone antagonist polypeptide, (3) said cellular component(s) and (4) combinations thereof to decrease said amount of said impurity,
wherein said impurity is a trisulfide isoform of said polypeptide.

2. A process for decreasing the amount of an impurity produced in recombinant production of a growth hormone antagonist polypeptide B-2036 of SEQ ID NO:1 in genetically modified host cells containing cellular component(s), the process comprising the step of:
   (a) contacting a chelating agent with a cell lysate or cell paste lysate comprising (1) said impurity, (2) said growth hormone antagonist polypeptide, (3) said cellular component(s) and (4) combinations thereof to decrease said amount of said impurity,
wherein said impurity is a des-phe isoform of said polypeptide.

3. The process of claim 1, wherein said chelating agent is selected from the group consisting of EDTA, EGTA, and DTPA.

4. The process of claim 3, wherein said chelating agent is EDTA.

5. The process of claim 1, wherein said chelating agent is provided in a buffer.

6. The process of claim 4, wherein said EDTA has an initial concentration from about 2 mM to about 10 mM.

7. The process of claim 5, wherein said buffer is selected from the group consisting of Tris, phosphate, HEPES, citric acid, triethylamine, and histidine.

8. The process of claim 7, wherein said buffer is Tris.

9. The process of claim 8, wherein said Tris buffer has an initial Tris concentration from about 1 mM to about 200 mM.

10. The process of claim 5, wherein after said contacting step (a) said buffer has a pH from about 6 to about 9.

11. The process of claim 1, wherein the temperature is maintained from about 0° C. to about 35° C.

12. The process of claim 11, wherein the temperature is maintained from about 2° C. to about 15° C.

13. The process of claim 2, wherein said chelating agent is selected from the group consisting of EDTA, EGTA, and DTPA.

14. The process of claim 13, wherein said chelating agent is EDTA.

15. The process of claim 2, wherein said chelating agent is provided in a buffer.

16. The process of claim 14, wherein said EDTA has an initial concentration from about 2 mM to about 10 mM.

17. The process of claim 15 wherein said buffer is selected from the group consisting of Tris, phosphate, HEPES, citric acid, triethylamine, and histidine.

18. The process of claim 17, wherein said buffer is Tris.

19. The process of claim 18, wherein said Tris buffer has an initial Tris concentration from about 1 mM to about 200 mM.

20. The process of claim 15, wherein after said contacting step (a) said buffer has a pH from about 6 to about 9.

21. The process of claim 2, wherein the temperature is maintained from about 0° C. to about 35° C.

22. The process of claim 21, wherein the temperature is maintained from about 2° C. to about 15° C.

* * * * *

```
                          SEQUENCE LISTING

<160> NUMBER OF SEQ ID NOS: 2

<210> SEQ ID NO 1
<211> LENGTH: 191
<212> TYPE: PRT
<213> ORGANISM: Homo sapiens

<400> SEQUENCE: 1

Phe Pro Thr Ile Pro Leu Ser Arg Leu Phe Asp Asn Ala Met Leu Arg
1               5                   10                  15

Ala Asp Arg Leu Asn Gln Leu Ala Phe Asp Thr Tyr Gln Glu Phe Glu
                20                  25                  30

Glu Ala Tyr Ile Pro Lys Glu Gln Lys Tyr Ser Phe Leu Gln Asn Pro
            35                  40                  45

Gln Thr Ser Leu Cys Phe Ser Glu Ser Ile Pro Thr Pro Ser Asn Arg
        50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
                100                 105                 110

Leu Leu Lys Asp Leu Glu Glu Lys Ile Gln Thr Leu Met Gly Arg Leu
            115                 120                 125

Glu Asp Gly Ser Pro Arg Thr Gly Gln Ile Phe Lys Gln Thr Tyr Ser
        130                 135                 140

Lys Phe Asp Thr Asn Ser His Asn Asp Ala Leu Leu Lys Asn Tyr
145                 150                 155                 160

Gly Leu Leu Tyr Cys Phe Asn Ala Asp Met Ser Arg Val Ser Thr Phe
                165                 170                 175

Leu Arg Thr Val Gln Cys Arg Ser Val Glu Gly Ser Cys Gly Phe
            180                 185                 190

<210> SEQ ID NO 2
<211> LENGTH: 191
<212> TYPE: PRT
<213> ORGANISM: Homo sapiens

<400> SEQUENCE: 2

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
                20                  25                  30

Glu Ala Tyr Ile Pro Lys Glu Gln Lys Tyr Ser Phe Leu Gln Asn Pro
            35                  40                  45

Gln Thr Ser Leu Cys Phe Ser Glu Ser Ile Pro Thr Pro Ser Asn Arg
        50                  55                  60

Glu Glu Thr Gln Gln Lys Ser Asn Leu Glu Leu Leu Arg Ile Ser Leu
65                  70                  75                  80
```

```
Leu Leu Ile Gln Ser Trp Leu Glu Pro Val Gln Phe Leu Arg Ser Val
            85              90                  95

Phe Ala Asn Ser Leu Val Tyr Gly Ala Ser Asp Ser Asn Val Tyr Asp
            100             105             110

Leu Leu Lys Asp Leu Glu Glu Gly Ile Gln Thr Leu Met Gly Arg Leu
            115             120              125

Glu Asp Gly Ser Pro Arg Thr Gly Gln Ile Phe Lys Gln Thr Tyr Ser
        130             135              140

Lys Phe Asp Thr Asn Ser His Asn Asp Asp Ala Leu Leu Lys Asn Tyr
145             150              155                          160

Gly Leu Leu Tyr Cys Phe Arg Lys Asp Met Asp Lys Val Glu Thr Phe
                165             170              175

Leu Arg Ile Val Gln Cys Arg Ser Val Glu Gly Ser Cys Gly Phe
            180             185              190
```